(12) United States Patent
Stulberg

(10) Patent No.: US 6,270,502 B1
(45) Date of Patent: Aug. 7, 2001

(54) METHODS AND INSTRUMENTS FOR PERFORMING RADIAL IMPACTING

(75) Inventor: S. David Stulberg, Chicago, IL (US)

(73) Assignee: Smith & Nephew, Inc., Memphis, TN (US)

(*) Notice: Subject to any disclaimer, the term of this patent is extended or adjusted under 35 U.S.C. 154(b) by 0 days.

(21) Appl. No.: 09/210,116

(22) Filed: Dec. 11, 1998

(51) Int. Cl.$^7$ ................................................. A61F 5/00
(52) U.S. Cl. ................................. 606/86; 606/92; 606/95
(58) Field of Search ................................. 606/86, 94, 92, 606/98, 90, 80, 170, 96; 623/22

(56) References Cited

U.S. PATENT DOCUMENTS

| | | |
|---|---|---|
| 4,921,493 | 5/1990 | Webb, Jr. et al. . |
| 5,047,035 | 9/1991 | Mikhail et al. . |
| 5,078,746 * | 1/1992 | Garner ................................. 606/86 |
| 5,171,275 | 12/1992 | Ling et al. . |
| 5,192,283 * | 3/1993 | Ling et al. ............................ 606/93 |
| 5,314,493 | 5/1994 | Mikhail . |
| 5,326,376 * | 7/1994 | Warner et al. ........................ 606/93 |
| 5,341,493 | 8/1994 | Yanai et al. . |
| 5,385,566 | 1/1995 | Ullmark . |
| 5,443,468 | 8/1995 | Johnson . |
| 5,470,336 | 11/1995 | Ling et al. . |
| 5,683,395 * | 11/1997 | Mikhail ................................ 606/89 |
| 5,718,707 * | 2/1998 | Mikhail ................................ 606/94 |
| 5,755,720 * | 5/1998 | Mikhail ................................ 606/94 |
| 5,788,704 * | 8/1998 | Timperley ............................ 606/95 |
| 5,800,437 * | 9/1998 | Gustilo et al. ....................... 606/86 |

FOREIGN PATENT DOCUMENTS

| | | |
|---|---|---|
| 0 555 004 A1 | 8/1993 | (EP) . |
| 0 711 535 A1 | 5/1996 | (EP) . |
| 0711535 A1 * | 5/1996 | (EP) ............................................ 606/86 |
| 0 595 956 B1 | 9/1998 | (EP) . |
| WO 96/09011 | 3/1996 | (WO) . |

OTHER PUBLICATIONS

Clive P. Duncan "Controversies in Total Hip Replacement", Oct. 1993.*

International Search Report in corresponding application #PCT/US99/28932.

Roser, Donath and Schnettler, "Histopathologische und histochemische Untersuchungen an unentkalkten Schliffpraparaten zur Knochen–defektheilung unter Verwendung allogener Transplantate und poroser Hydroxylapatitkeramik–Implantate," Osteo. Int. 2, 128–134 (1994).

(List continued on next page.)

Primary Examiner—Henry J. Recla
Assistant Examiner—Anthony S. King
(74) Attorney, Agent, or Firm—Camilla C. Williams; Kilpatrick Stockton LLP

(57) ABSTRACT

A radial impacting technique involves using a set of progressively larger radial impactors to pack a medullary canal in a radial direction toward the cortex. For revision cases, graft material, which may be either synthetic or bone graft material, is added into the medullary canal after the previously installed implant has been removed. Packing the medullary canal in the radial direction, as opposed to the conventional approach of packing in a distal direction, provides superior results. The radial impactors are preferably cannulated and may also have holes to assist in the removal of fluids from within the medullary canal. The profile impactors may be either cannulated or non-cannulated and prepare the medullary canal for receipt of the implant.

83 Claims, 18 Drawing Sheets

OTHER PUBLICATIONS

Engelbrecht and Heinert, "Klassifikation und Behandlungsrichtlinien von Knochensubstanzverlusten bei Revisionsoperationen am Huftgelenk–mittelfristige Ergebnisse," *Primar– und. Revisionsalloarthroplastik*, (Springer–Verlag, Berlin, Heidelberg) 189–201 (1987).

Baldursson, et al., "Instability and Wear of Total Hip Prosthesis Determined with Roentgen Stereophotogrammetry," *Arch. Orthop. and Trauma Surg.*, 95:257–263 (1979).

Eldridge, et al., "Massive Early Subsidence Following Femoral Impaction Grafting," *The Journal of Arthroplasty*, 12(5) 535–540 (1997).

Elting, et al., "Preliminary Report of Impaction Grafting for Exchange Femoral Arthroplasty," *Clinical Orthopaedics*, 319:159–167 (1995).

Franzén, et al., "Early Migration of Femoral Components Revised with Impacted Cancellous Allografts and Cement," *J. Bone Joint Surg.*, 77B:862–864 (1995).

Garbuz, et al., "Classification and Reconstruction in Revision Acetabular Arthroplasty with Bone Stock Deficiency," *Clinocal Orthopaedics and Related Research*, 323:98–107 (1996).

Gie, et al., "Impacted Cancellous Allografts and Cement for Revision Total Hip Arthoplasty," *J. Bone Joint Surg.*, 75B–14–21 (1993).

Gie, et al., "Contained Morselized Allograft in Revision Total Hip Arthroplasty," The *Orthopedic Clinics of North America*, 24:717–725 (1993).

Gruen, et al., "Modes of Failure of Cemented Stem–Type Femoral Components. A Radiographic Analysis of Loosening," *Clinical Orthopaedics and Related Research*, 141:17–27 (1979).

Gustilo, et al., "Revision Total Hip Arthroplasty with Titanium Ingrowth Prosthesis and Bone Grafting for Failed Cemented Femoral Component Loosening," *Clinical Orthopaedics and Related Research*, 235:111–119 (1988).

Heekin, et al., "Morselized Allograft in Acetabular Reconstruction," *Clinical Orthopaedics and Related Research*, 319:184–190 (1995).

Kärrholm, Johan, "Stem Migration and Bone Remodeling After Impaction of Cancellous Allograft in Revision Surgery," first prize Poster Exhibit EFORT, Spain (1997).

Kärrholm, et al., "Radiostereometry of Hip Prostheses. Review of Methodology and Clinical Results," *Clin. Orthop.*, 344:94–110 (1997).

Kärrholm, Johan, et al., "Subsidence of a Non–Polished Stem in Revisions of the Hip Using Impaction Allograft," 81B(1):135–142 (1999).

Levai and Boisgard, "Acetabular Reconstruction in Total Hip Revision Using a Bone Graft Substitute," *Clinical Orthopaedocs and Related Research*, 330:108–114 (1996).

Malchau and Herberts, "Prognosis of total hip replacement," *International Journal of Risk & Safety in Medicine*, Special Issue: 2th European Conference on Post Marketing Surveillance for Medical Implants, 8:27–45 (1996).

Masterson, et al., "The Cement Mantle in the Exeter Impaction Allografting Technique–A Cause for Concern," *The Journal of Arthroplasty*, 12(7):759–764 (1997).

Meding, et al., "Impaction Bone–Grafting Before Insertion of a Femoral Stem with Cement in Revision Total Hip Arthroplasty," *The Journal of Bone and Joint Surgery*, 79A(12):1834–1841 (Dec. 1997).

Mjoberg, "Loosening of the Cemented Hip Prosthesis. The Importance of Heat Injury," *Acta. Orthop. Scand.*, (Suppl 221) 57:1–40 (1986).

Namba, et al., "Bipolar Revisions with Bone–Grafting for Cavitary and Segmental Acetabular Defects," *The Journal of Arthroplasty*, 9(3):263–268 (1994).

Nivbrant, et al., "Increased Subsidence of Uncemented Femoral Stems in Hip Revisions with Impaction Grafting," *Acta. Orthop. Scand. Proceedings Dissertations* Suppl. 274(68):79–80 (1997).

Ornstein, et al., "Prosthetic Migration During 1.5 Years After Hip Revision with Impacted Morselized Allograft Evaluated by RSA," *Trans. Orthop. Res. Soc.*, 43rd Annual Meeting, San Francisco 843 (1997).

Simon, et al., "Impaction Cancellous Grafting of the Femur in Cemented Total Hip Revision Arthroplasty," *J. Bone Joint Surg.*, 73–B:S73 (1991).

Slooff, et al., "Bone grafting in total hip replacement for acetabular protrusion," *Acta Orthop. Scand.*, 55:593–595 (1984).

Slooff, et al., "Acetabular and Femoral Reconstruction with Impacted Graft and Cement," *Clinical Orthopaedocs and Related Research*, 323:108–115 (1996).

Stulberg, "Radial Impaction Grafting in Revision THA: A New Technique and Results Using Rough Surfaced Femoral Stems of Variable Lengths and Neck Offsets," Northwestern University Hospital, Chicago, Illinois (Apr. 24, 1998).

Thanner, et al., "Evaluation of Boneloc®. Chemical and Mechanical Properties and a Randomized Clinical Study of 30 Total Hip Arthroplasties," *Acta. Orthop. Scand.*, 66(3):207–214 (1995).

Verdonschot, et al., "Acrylic Cement Creeps But Does Not Allow Much Subsidence of Femoral Stems," *J. Bone Joint Surg.*, 79–B:665–669 (1997).

Weightman, et al., "The Mechanical Properties of Cement and Loosening of the Femoral Component of Hip Replacements," *J. Bone Surg.*, 69–B:558–564 (1987).

Fourteenth Annual "Current Concepts in Joint Replacement," A Continuing Medical Education Program presented by The Mt. Sinai Medical Center and sponsored by the Case Western Reserve University School of Medicine (Dec. 11–13, 1997).

DePuy, "Total Hip Products—The Solution System" catalogue A–15 (1991).

Contour™ Acetabular Rings Surgical Technique catalogue, pp. 1–15, Smith & Nephew (1998).

Innomed, "Instruments for Orthopedic Surgery Designed by Orthopedic Surgeons since 1987," catalogue (undated).

Zimmer CPT® Collarless Polished Taper promotional brochure (undated).

The CPT Revision Hip System Surgical Technique "Collarless Polished Taper," developed in conjunction with Mr. R.S.M. Ling, MA, BM (OXON), et al. (undated).

Howmedica/Stryker EXETER X–Change total hip system (undated).

Osteonics Restoration–C product (undated).

Biomet Bi–Metric product (undated).

\* cited by examiner

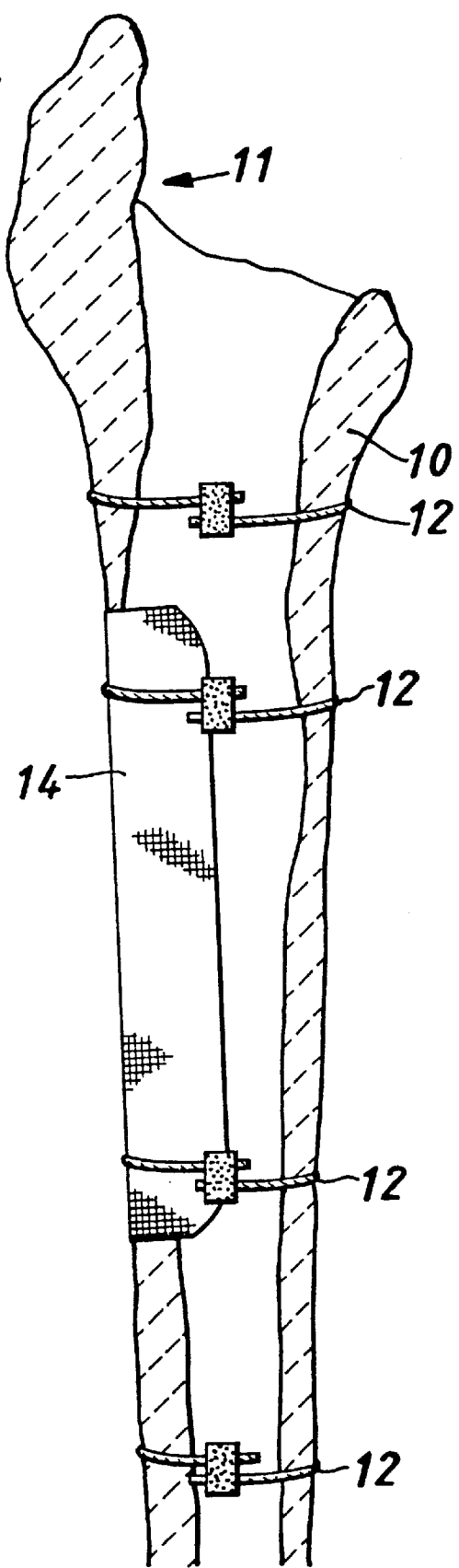

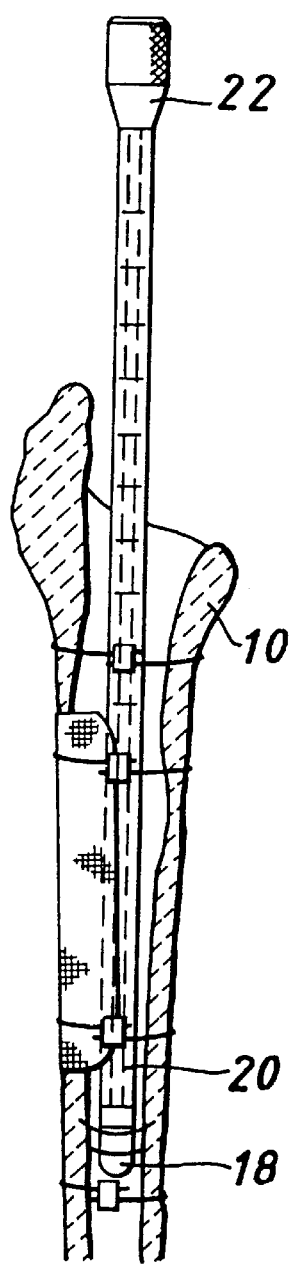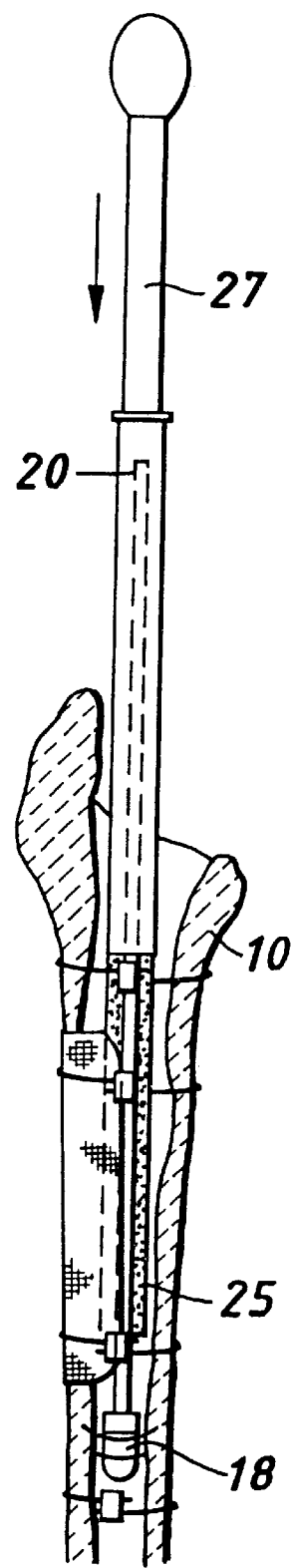

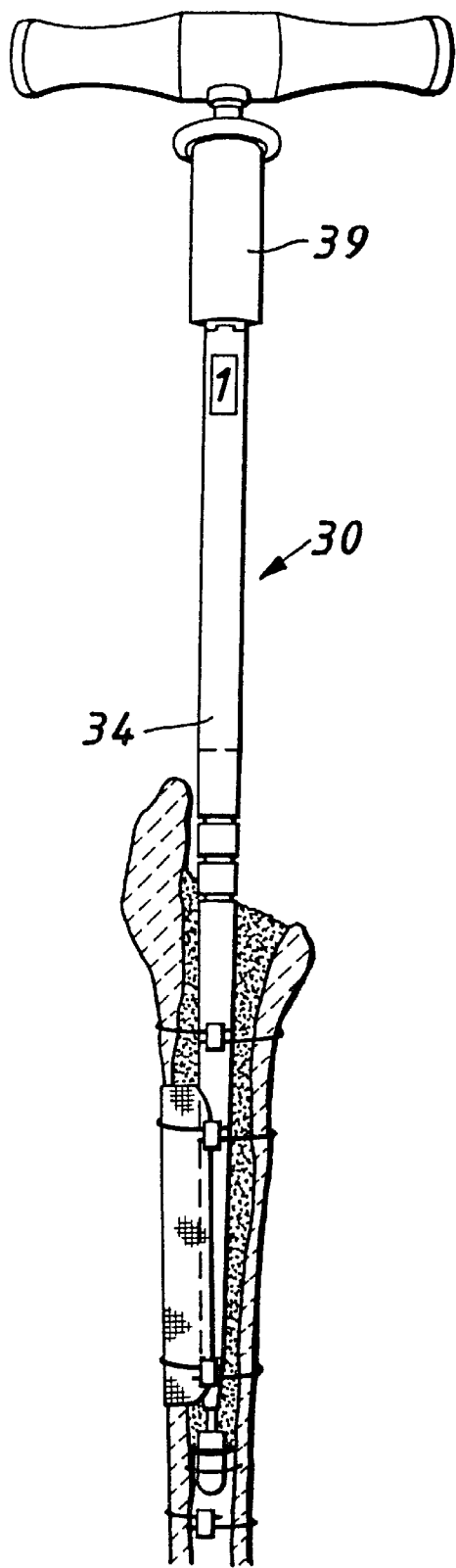
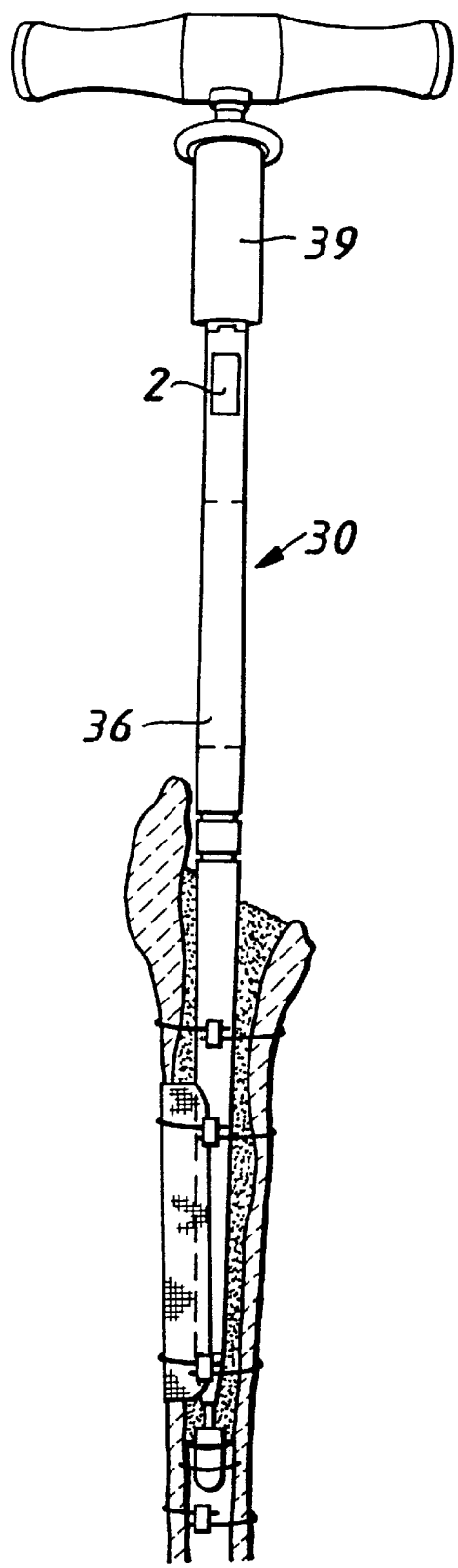

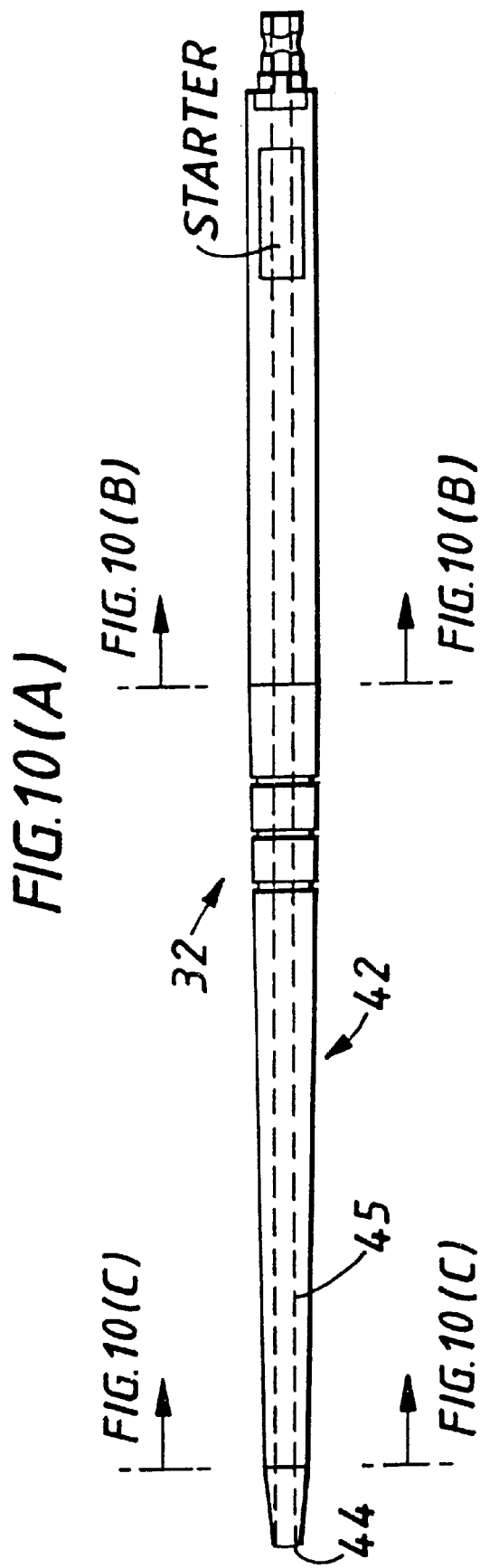

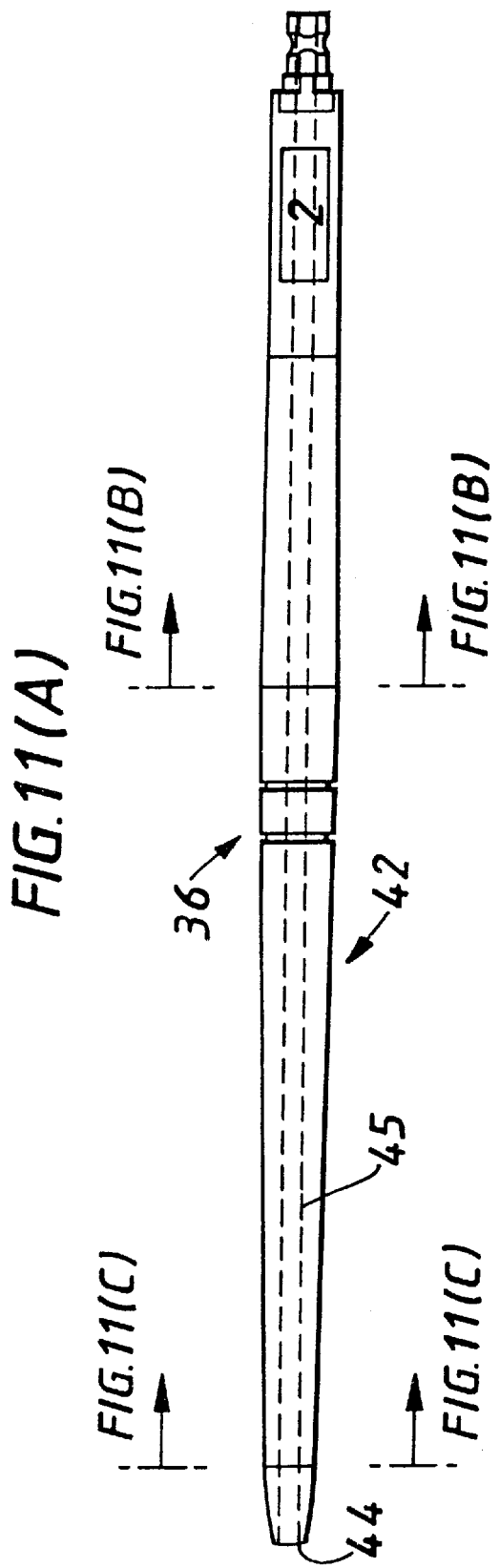

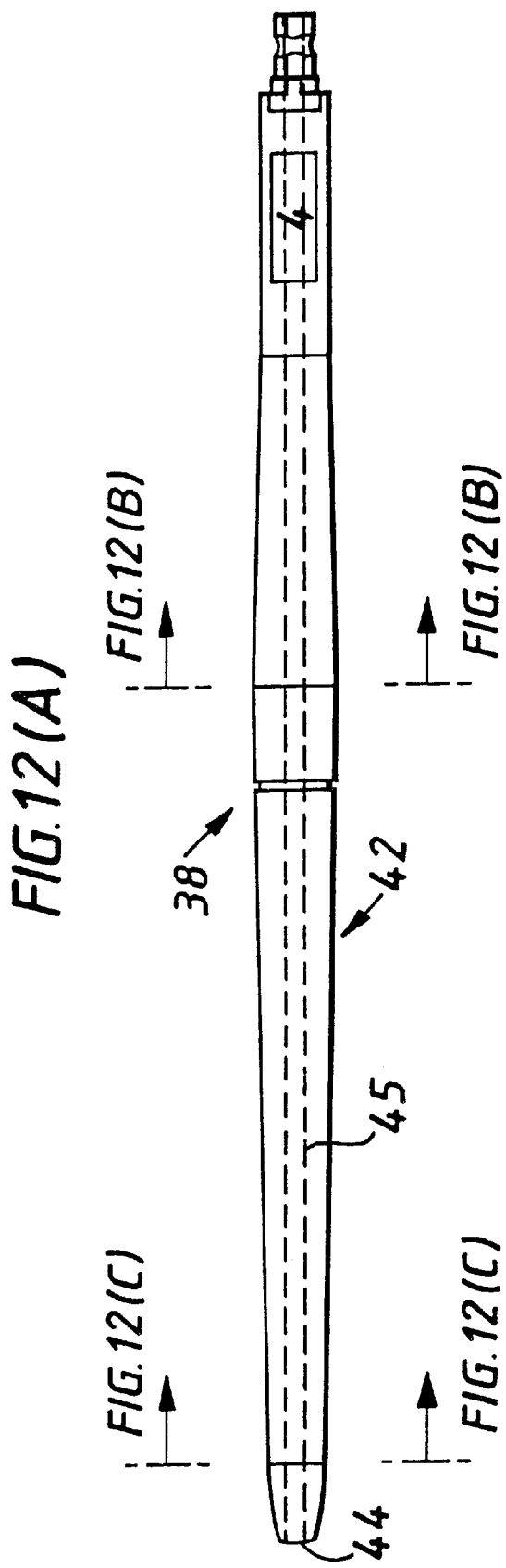
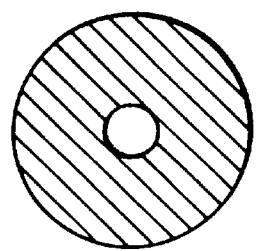
FIG.12(A)
FIG.12(B)
FIG.12(C)

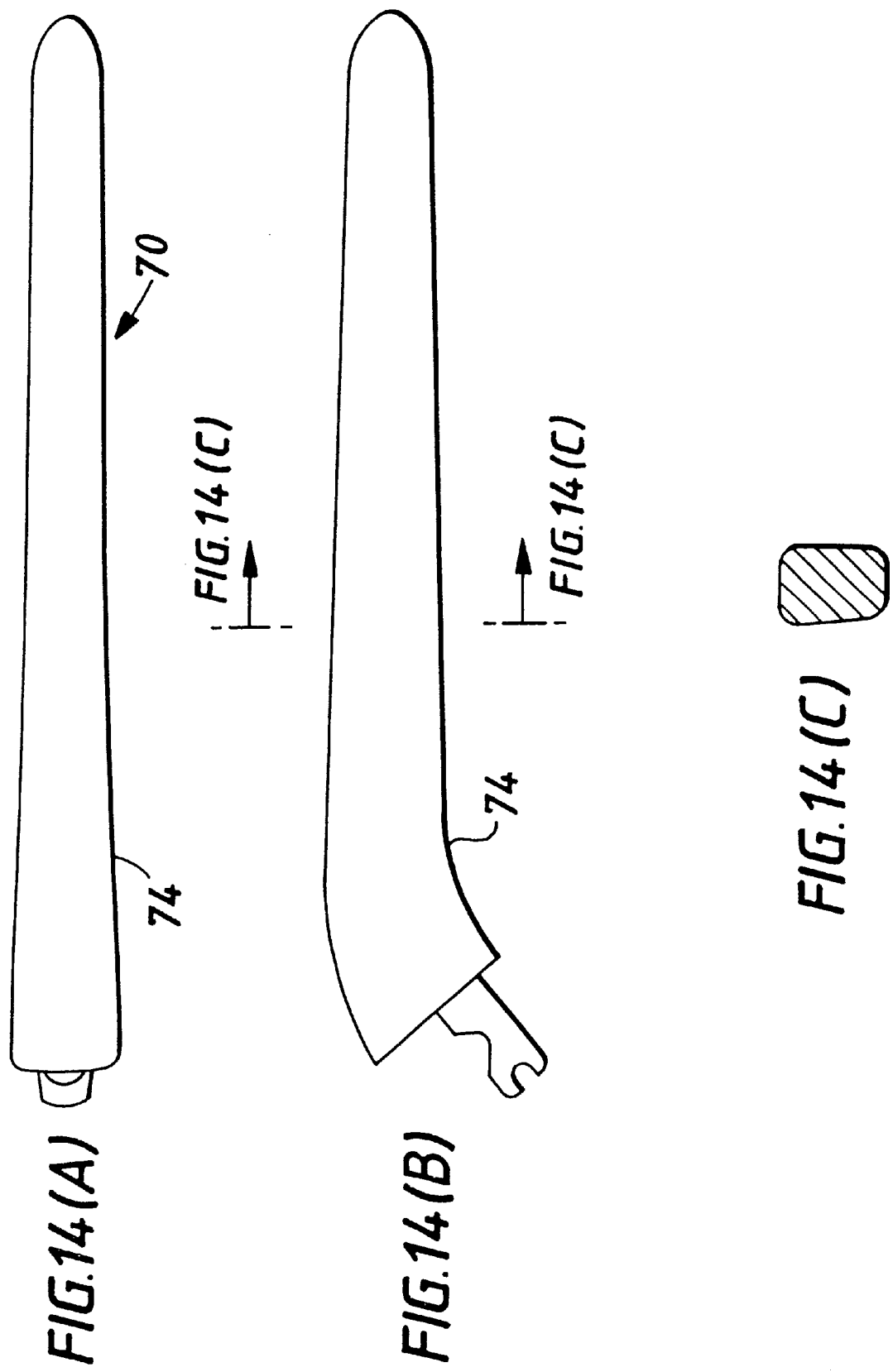

FIG. 16.
FIG. 17.
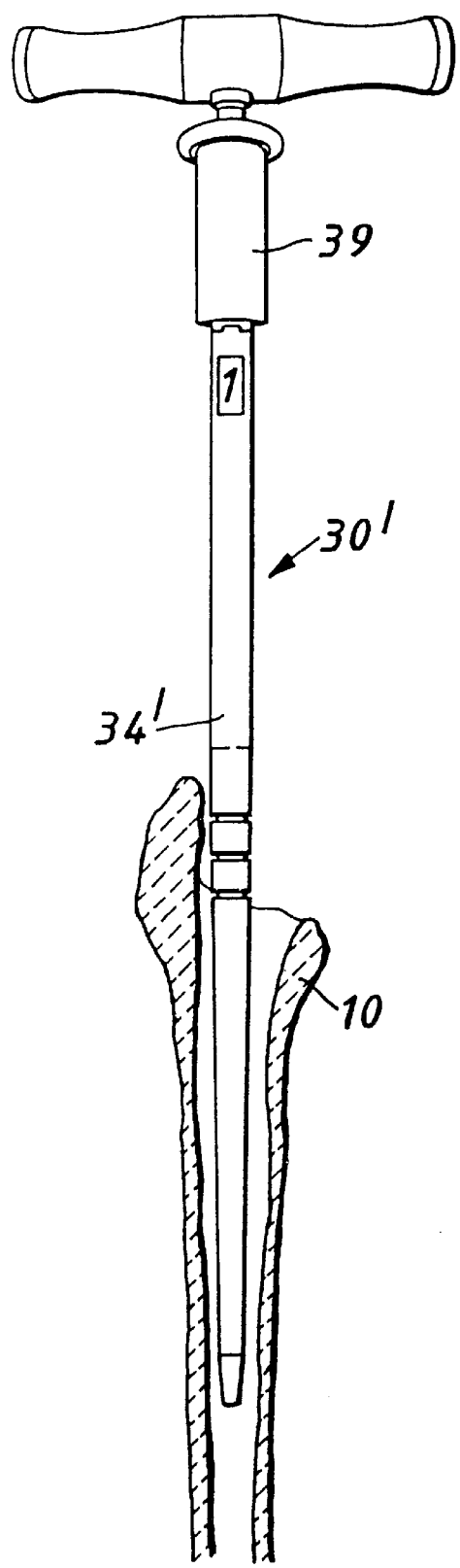
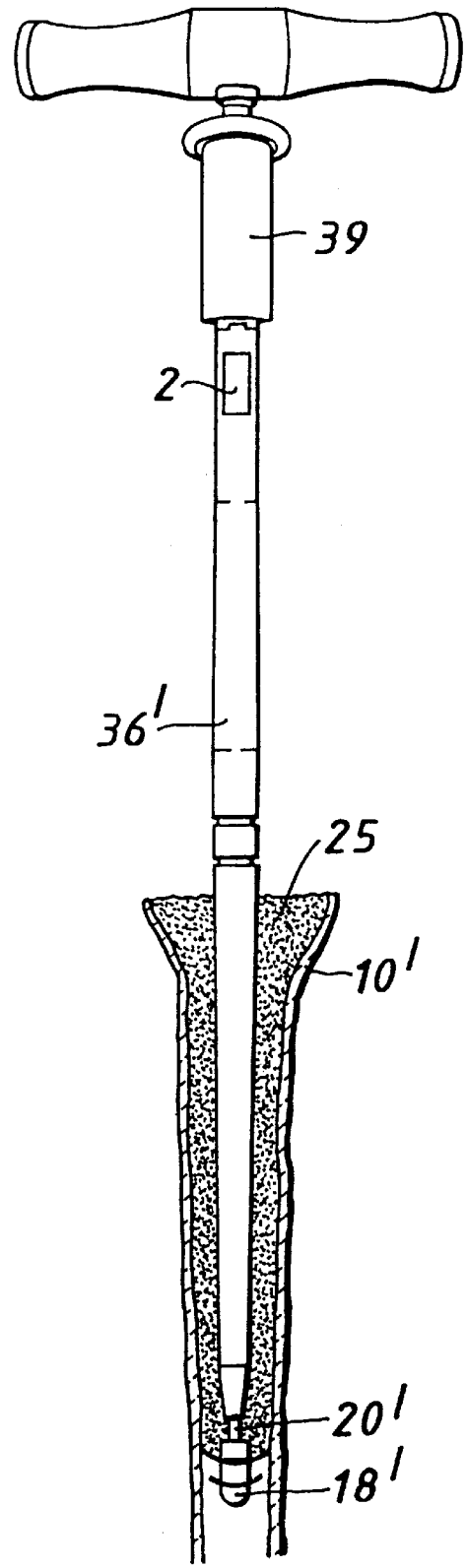

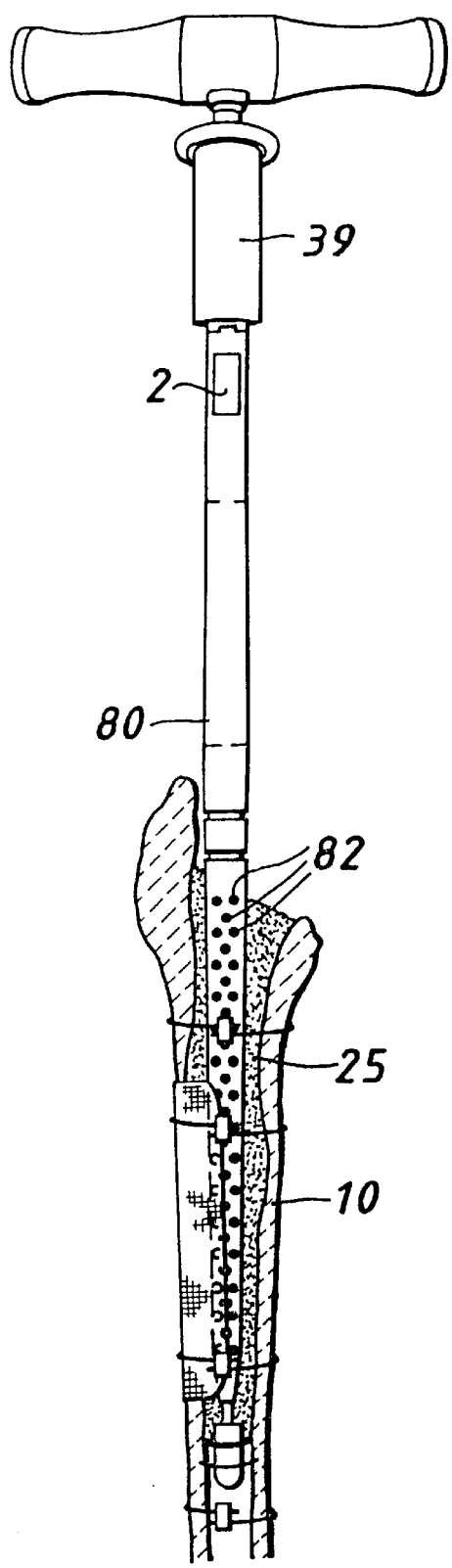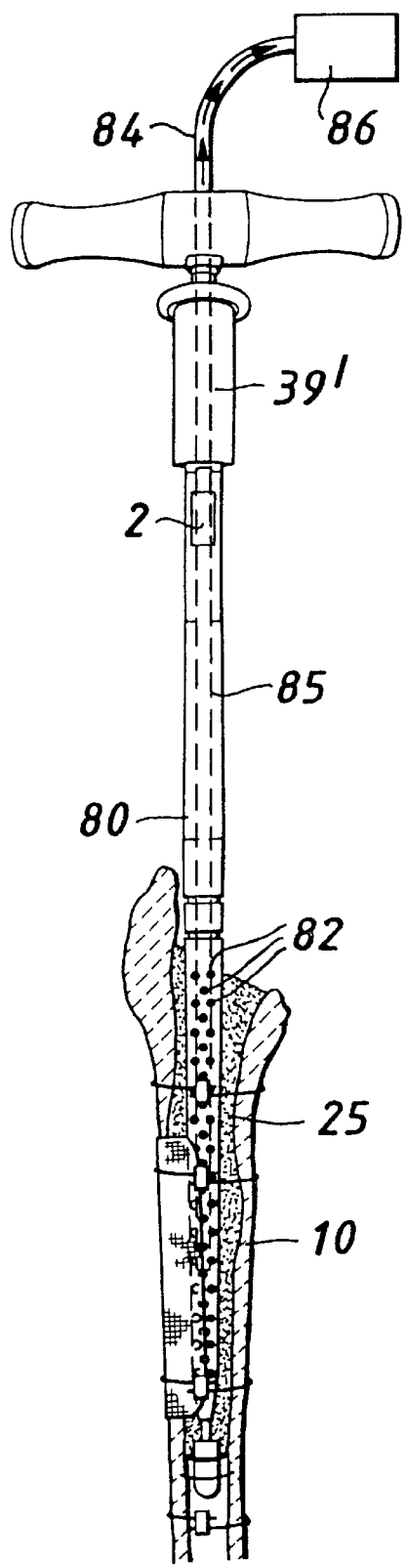

METHODS AND INSTRUMENTS FOR PERFORMING RADIAL IMPACTING

FIELD OF THE INVENTION

The present invention relates generally to methods and instruments for performing radial impacting and, more particularly, to methods and instruments for preparing a bone for arthroplasty by packing the medullary canal in a radial direction.

BACKGROUND OF THE INVENTION

A joint within the human body is a juncture between two or more bones or other skeletal parts. The ankle, knee, hip, elbow, shoulder, and fingers are just a few examples of the multitude of joints found within the body. As should be apparent from the above-listed examples of joints, many of the joints permit relative motion between the bones, such as a sliding, gliding, hinge, or ball-and-socket movements. For instance, the ankle permits a hinge movement, the knee allows a combination of hinge and gliding movements, and the shoulder and hip permit movement through a ball-and-socket arrangement.

The joints in the body are stressed or can be damaged in a variety of ways. For example, a gradual wear and tear is imposed on the joints just through the continuous use of the joint over the years. The joints that permit motion have cartilage positioned between the bones providing lubrication to the motion and also absorbing some of the forces directed to the joint. Over time, the normal use of a joint may wear down the cartilage and bring the moving bones in direct contact with each other. In contrast to normal use, a trauma to a joint, such as the delivery of a large force, may cause considerable damage to the bones, the cartilage, or to other connective tissues, such as tendons or ligaments.

Arthropathy, a term referring to a disease of the joint, is another way in which a joint may become damaged. Perhaps the best known joint disease is arthritis, which generally refers to a disease or inflammation of a joint that results in pain, swelling, stiffness, instability, and often deformity. There are many different forms of arthritis, with osteoarthritis being the most common and resulting from the wear and tear of a cartilage within the joint. Another type of arthritis is osteonecrosis, which is caused by the death of part of the bone due to a loss of blood supply. Other types of arthritis are caused by trauma to the joint while others, such as rheumatoid arthritis, Lupus, and psoriatic arthritis, destroy cartilage and are associated with inflammation of the joint lining.

The hip joint is one of the joints that is commonly afflicted with arthropathy. The hip joint is a ball and socket joint that joins the femur or thigh bone with the pelvis. The pelvis has a semi-spherical socket called the acetabulum for receiving a ball-shaped head of the femur. Both the head on the femur and the acetabulum are coated with cartilage for allowing the femur to move easily within the pelvis. Other joints commonly afflicted with arthropathy include the spine, knee, shoulder, elbow, carpals, metacarpals, and phalanges of the hand.

Arthroplasty, as opposed to arthropathy, commonly refers to the making of an artificial joint. In severe cases of arthritis and other forms of arthropathy, such as when the pain is overwhelming or when a joint has a limited range of mobility, a partial or total replacement of the joint with an artificial joint may be justified. The procedure for replacing the joint varies, of course, with the particular joint in question but in general involves replacing a terminal portion of the afflicted bone with a prosthetic implant and inserting a member to serve as a substitute for the cartilage. The prosthetic implant is formed of a rigid material that becomes bonded with the bone and provides strength and rigidity to the joint and the cartilage substitute member is chosen to provide lubrication to the joint and to absorb some compressive forces. Suitable materials for the implant include metals and composite materials, such as titanium, cobalt chromium, and zirconia ceramic, and suitable materials for the cartilage substitute member includes polyethylene. A cement may also be used to secure the prosthetic implant to the host bone.

A total hip replacement, for example, involves removing the ball-shaped head of the femur and inserting a stem implant into the center of the bone, which is referred to as the medullary canal or the marrow of the bone. The stem implant may be cemented into the medullary canal or may have a porous surface for allowing the bone to heal directly to the implant. The stem implant has a neck and a ball-shaped head which are intended to perform the same functions as a healthy femur's neck and ball-shaped head. A polyethylene cup is inserted into the acetabulum and has a socket for receiving the head on the stem implant.

Unfortunately, some patients who have undergone partial or total joint replacement require revision surgery. Revision surgery may be required soon after the primary surgery or may not be needed for years. Revision surgery may be required for any one of a number of reasons. For one, fixation of the joint may become compromised. A trauma to the joint may have resulted in the loosening or the loosening of the joint may have been caused by other factors, such as an insufficient bond between the implant and the host bone. The loosening of an implant can be quite painful and also can pose a danger to the patient. For instance, movement of the loose implant within the bone may fracture the bone itself.

Revision surgery may be necessary for other reasons. For example, particle debris from the cartilage substitute member or even from any of the other implants may cause osteolysis in the patient. In general, osteolysis is the body's natural immune response to foreign objects which results in inflammation and pain in the joint. Another reason why revision surgery may be necessary is due to death of part of the bone. A bone requires stress in order to remain strong and a bone that is not stressed will become weak and fragile. The insertion of an implant may stress shield portions of the bone whereby these portions no longer receive the stress that it requires in order to remain strong. Another reason to perform revision surgery is to take advantage of advancements in prosthesis design. Thus, for any number of reasons, revision surgery may be necessary or desirable for a patient.

Revision surgery is more complicated than the primary partial or total joint replacement since it requires the removal of the previously inserted stem implant and the reintroduction of another stem implant. When the stem implant is removed, a significant portion of the surrounding tissue is removed along with the implant. If cement was used to secure the original implant, then additional tissue is normally removed to ensure that all of the cement has been removed from within the medullary canal. During a revision surgery, this void left by the removal of the surrounding tissue must be filled in order to allow the stem implant to bond with the host bone.

Dr. Ling et al. (collectively "Ling") have developed a surgical technique for the revision of a hip system. An example of this system is the CPT® (collarless polished taper) Revision Hip System, marketed by Zimmer, Inc. of Warsaw, Ind. Reference may also be made to U.S. Pat. Nos. 5,047,035, 5,192,283, 5,314,493, 5,326,376, 5,470,336, 5,683,395, 5,718,707, and 5,755,720 which are fairly representative of conventional approaches to revision surgery and to arthroplasty in general and which are incorporated herein by reference.

The CPT® technique involves the removal of the stem implant, any fibrous membrane, and bone cement and then thoroughly lavaging the femoral canal. A guide wire is threaded into a stiff intramedullary plug and the plug and guide wire are placed within the medullary canal with the plug firmly seated within the femur. The guide wire is inserted so that it is aligned with a longitudinal axis of the femur. A small amount of morselized allograft is inserted into the femur and packed until the distal one third of the proximal femur has been filled.

Next, a tamping process is performed which packs additional allograft material into the medullary canal until the planned size for the stem implant is reached. This tamping process begins with the insertion of a relatively large cannulated tamp approximately two sizes larger than the final component. A force is applied to the tamp, such as from a hammer, until the tamp is fully seated on the graft material. A smaller tamp size is selected and additional graft material is introduced into the medullary canal. A force is applied to this smaller sized tamp until it is fully seated on the allograft material. This tamping process is repeated with progressively smaller tamp sizes until the appropriate size is firmly seated. Thus, with this process, the allograft material is distally packed into the medullary canal with tamps of progressively smaller sizes until the appropriate size is firmly seated.

After using the progressively smaller tamps, final filling of the medullary canal is completed with proximal packers with the final tamp remaining in place. After proximal packing of the medullary canal is completed, the guide wire is removed and the tamp is left in place. Blood pooled at the distal end of the stem may be extracted with suction applied to the guide wire hole in the tamp. The tamp is then removed just immediately prior to insertion of cement into the medullary canal. A cement gun with a small diameter nozzle cut off to the length of the stem is used to inject cement into the narrow distal stem area. A second larger nozzle is then used to complete filling of the proximal femur and to pressurize the cement. The stem is inserted and pressure is maintained until the cement has polymerized.

The CPT® technique suffers from a number of the same limitations as the primary cases. Stems inserted with the CPT® technique, for example, have a fairly high rate of subsidence. The stem implant does not remain in place but rather migrates within the cement, which is excessive, results in loosening of the stem. A loose stem implant, as discussed above, is causes pain and may result in fracture of the host bone. Subsidence of the stem implant may also introduce a discrepancy in length between the limbs, which is especially serious if the differences in lengths are in the femur or tibia. A loose stem implant is also problematic since it increases the chance that particle debris from the cement is generated, thereby increasing the rate of osteolysis.

Another limitation of the CPT® technique is that the results of partial or total joint replacements vary considerably between surgeons due to variability in the packing of the medullary canal. At present, a surgeon has no objective indication as to whether the medullary canal is sufficiently packed with graft material. Consequently, even though surgeons may follow the same procedure, the amount of graft material introduced into the medullary canal and the density of the graft material varies between surgeons, with some surgeons more tightly packing the medullary canal than other surgeons. Some surgeons may be reluctant to pack the medullary canal as tightly as possible since in doing so the surgeon may inadvertently fracture the host bone. Even with a single surgeon, the results of a surgery will likely vary since the surgeon cannot accurately gauge the density and distribution of the graft material within the medullary canal.

SUMMARY OF THE INVENTION

The present invention addresses the problems described above by providing methods, instruments, and collections of instruments that are used to prepare a bone for arthroplasty. The instruments have a working surface that is used to pack the medullary canal in a radial direction toward the cortex of the bone. The instruments preferably have a smooth working surface and are tapered at their insertion ends. The instruments may be cannulated or non-cannulated, be used during primary or revision surgeries, and may be used with or without graft material.

According to one aspect, the instruments include a plurality of radial impactors for preparing a bone for arthroplasty. Each radial impactor has a smooth working surface, preferably has a tapered insertion end, and preferably has a circular cross-section. A relatively small diameter radial impactor is first inserted into the medullary canal and packs the medullary canal in a radial direction toward the cortex. The first radial impactor forms a space in the medullary canal of a first size. A second radial impactor, which is larger in diameter than the first radial impactor, is then inserted into the medullary canal to pack the medullary canal in the radial direction. The second radial impactor packs the medullary canal denser than the first radial impactor and increases the diameter of the space in the medullary canal. Progressively larger sized radial impactors are inserted into the medullary canal to pack the medullary canal in the radial direction until the size of the space within the medullary canal approximates the space required for the prosthetic implant.

Depending upon the shape of the prosthetic implant, one or more profile impactors may be inserted into the medullary canal following the insertion of the radial impactors. The profile impactors have a shape that approximates the portion of the implant that is inserted into the medullary canal. At least one profile impactor is inserted into the medullary canal to prepare the medullary canal for receipt of the prosthetic implant. The size of the profile impactor preferably corresponds with the size of the last used radial impactor.

A series of profile impactors may be used to prepare the medullary canal of a bone for arthroplasty. As with the radial impactors, a smaller sized profile impactor is first inserted into the medullary canal following by successively larger profile impactors. The profile impactors perform radial packing of the medullary canal and also size the medullary canal for the corresponding prosthetic implant. The series of profile impactors may be used in conjunction with radial impactors or instead of the radial impactors. Furthermore, the profile impactors may be cannulated or non-cannulated, used in primary or revision surgeries, and may be used with or without graft material.

The methods, instruments, and collections of instruments therefore may be used either during primary or revision surgery. For revision surgery, the previously installed implant must be removed from within the medullary canal along with any remaining cement. Because of a large void left after the implant and other surrounding materials have been removed, graft material likely will need to be added. The graft material may be any suitable material, such as bone graft material or a synthetic graft material. For revision cases, a guide wire and intramedullary plug are preferably inserted into the medullary canal and the guide wire is aligned with a central axis of the bone. A distal portion of the medullary canal is filled with graft material and the graft material is compressed in a distal direction along the length of the guide wire. The radial impactors are preferably cannulated, although not necessarily, and are guided into the medullary canal with the guide wire. The profile impactors may also be cannulated, but as with the radial impactors, may be non-cannulated in design. For example, the guide wire may be removed from within the medullary canal prior to the insertion of the one or more profile impactors.

After the medullary canal has been prepared, a suitable prosthetic implant is selected and is inserted into the medullary canal. The prosthetic implant may be secured to the host bone in any suitable manner, such as through bonding due to porous surfaces on the implant or through cement.

According to another aspect of the invention, the instruments has a plurality of holes. These holes are preferably sized and shaped to receive fluids from within the medullary canal. These fluids interfere with the optimal packing of the medullary canal and may be drawn into the instruments and out of the medullary canal through the central bore or aperture in cannulated instruments.

Accordingly, it is an object of the present invention to provide improved procedures, methods, and instruments for preparing a bone for arthroplasty.

It is another object of the present invention to provide improved procedures, methods, and instruments for performing revision surgery.

It is a further object of the present invention to provide improved procedures, methods, and instruments for the implantation of a replacement hip prosthesis.

It is still a further object of the present invention to provide methods and instruments for radially packing the medullary canal of a bone.

It is yet another object of the present invention to provide improved processes, methods, and instruments for more tightly packing the medullary canal of a bone.

It is yet a further object of the present invention to provide methods and instruments for improving the incorporation of graft material to the host bone.

It is yet another object of the present invention to provide methods and instruments for implanting a prosthetic implant that provides more uniform results.

Other objects, features, and advantages of the present invention will become apparent with respect to the remainder of this document.

BRIEF DESCRIPTION OF THE DRAWINGS

The accompanying drawings, which are incorporated in and form a part of the specification, illustrate preferred embodiments of the present invention and, together with the description, disclose the principles of the invention. In the drawings:

FIG. 1 is a partial schematic view of a femur having undergone preoperative planning;

FIG. 2 is a partial schematic view of a femur having a guide rod and plug inserted into the medullary canal;

FIG. 3 is a partial schematic view of a femur having a graft delivery syringe inserted into the medullary canal;

FIGS. 5(A) to 5(C) are partial schematic views of a femur having radial impactors of increasingly larger sizes introduced into the medullary canal;

FIG. 10(A) is a side view and FIGS. 10(B) and 10(C) cross-sectional views at two positions along a radial impactor of a first size;

FIG. 11(A) is a side view and FIGS. 11(B) and 11(C) are cross-sectional views at two positions along a radial impactor of a second size;

FIG. 12(A) is a side view and FIGS. 12(B) and 12(C) are cross-sectional views at two positions along a radial impactor of a third size;

FIGS. 14(A), 14(B), and 14(C) are top, side, and cross-sectional views, respectively, of a profile impactor of a second size;

FIG. 16 is a partial schematic view of a femur and a radial impactor inserted into the medullary canal for use during a primary case without graft material;

FIG. 17 is a partial schematic view of a tibia and a radial impactor inserted into the medullary canal;

FIG. 20(A) is a side view of a radial impactor according to a third embodiment of the invention, the radial impactor having holes for the removal of fluids; and FIG. 20(B) is a side view of the radial impactor of FIG. 20(A) having fluid withdrawn from the medullary canal.

DETAILED DESCRIPTION

Figure 4:
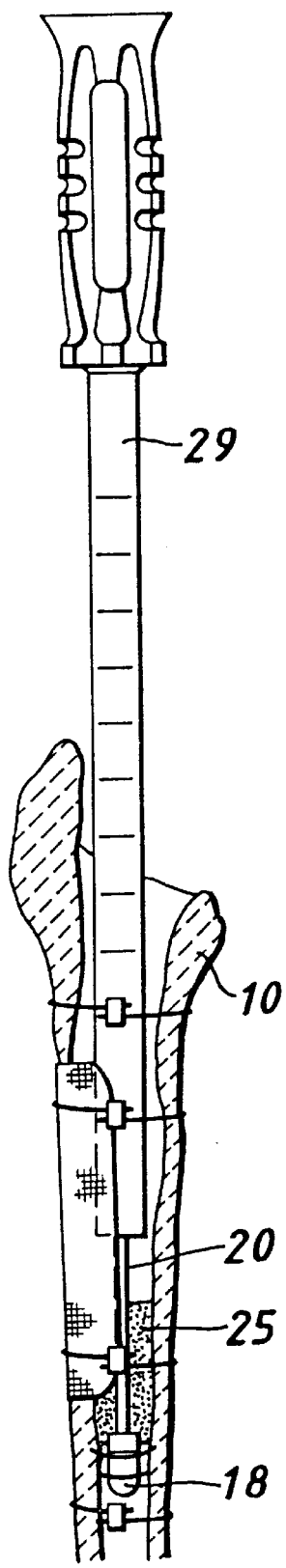
FIG. 4 is a partial schematic view of a femur having a canal filler inserted into the medullary canal.

Reference will now be made in detail to preferred embodiments of the invention, non-limiting examples of which are illustrated in the accompanying drawings.

I. Overview

In general, methods, techniques, and instruments according to a preferred embodiment of the invention prepare a bone for arthroplasty by packing the medullary canal in a radial direction toward the cortex of the bone. Conventional techniques, as discussed above, rely upon a series of progressively smaller tamps to distally pack the medullary canal with graft material. With the invention, in contrast, a series of progressively larger impactors are inserted into the medullary canal to pack the medullary canal in the radial direction toward the cortex. The radial packing of the medullary canal may supplement and be used after a distal packing of the medullary canal. An impactor of a size smaller than a prosthetic implant is selected and is inserted into the medullary canal. Progressively larger impactors are then inserted so as to continue to pack the medullary canal in the radial direction. The methods, instruments, and techniques according to the invention may be used with or without graft material, during primary or revision surgeries, and may be cannulated or non-cannulated. Furthermore, the methods, instruments, and techniques according to the invention may be adapted to any long bone, such as but not limited to the femur, fibula, tibia, radius, ulna, or humerus.

II. Femoral Revision Example

An example of the invention will now be discussed with reference to performing revision arthroplasty on a femur. A hip prosthesis is particularly vulnerable to the shifting or compression of the implant due to the large forces which are applied to the hip prosthesis during use. As will become more apparent from the description below, the invention is not limited to only revision cases but also has applications to primary arthroplasty surgery as well as arthroplasty with other joints.

With reference to FIG. 1, a femur 10 is shown which has completed preoperative planning. The femur 10 in this example previously had a stem implant for a prosthetic hip joint. The preoperative planning included removal of the stem implant using a surgical technique that minimizes loss of bone stock. Preferably, at least a portion of the femoral neck 11 is preserved during removal of the implant and also during removal of any bone cement within the femur. All cement is preferably removed from any portion of the femur that will later receive the new prosthetic implant. If well-fixed cement is present distal to that portion of the femur, it may be left in place and used to buttress a canal plug graft restrictor. As is typical with all revision hip surgeries, adequate exposure of the femur will ensure the safe removal of cement. Consequently, it may be appropriate to expose the entire shaft of the femur in order to avoid penetration or fracture of the femur. Complete removal of any fibrous membrane that is present ensures future successful attachment of graft material to the femur 10.

Preoperative planning is required for the precise reconstruction and restoration of the hip joint. The surgeon preferably acquires preoperative A–P and lateral radiographs of the hip joint. The surgeon should also identify any bony defects and classify these defects. Because the cortical shell of the femur 10 may be very thin and susceptible to fracture, the surgeon preferably places cerclage wires 12 around the femur 10 before any graft material is packed. Any uncontained defect may be covered with a wire mesh 14 retained with the cerclage wires 12 or with fracture plates. On-lay grafting can be advantageous in severe osteopenic cases. The cerclage wires 12 and wire mesh 14 should extend just beyond an anticipated point of distal-most packing. If no fractures occur during the packing and cementing, and if the surgeon desires, the cerclage wires 12 and wire mesh 14 may be removed prior to closure.

To ensure that all cement and fibrous tissue has been removed, the femur may be manually reamed with straight reamers. Reaming the femur allows the surgeon to determine the desired length of the prosthetic implant, which in this case would be a femoral stem, and a diameter of the femoral canal into which graft material will be placed. The surgeon preferably uses reamers of increasing diameters until the cortex is reached. Once the diameter of the femoral canal is known, the surgeon can estimate the likely thickness of the graft material.

With reference to FIG. 2, a guide wire 20 and intramedullary plug 18 that most closely approximates the size of the reamed intramedullary canal are then inserted with an insertion tool 22. The plug 18 is preferably inserted into the intramedullary canal at a point two centimeters beyond a tip of a prosthetic implant to be inserted. The plug 18 should be able to withstand impaction forces and additional fixation may be performed using cement or temporary transfemoral fixation with a K-wire. A distal sizer may be used to determine the adequate size of the plug 18.

For revision cases, graft material 25 is inserted into the medullary canal of the femur 10. The invention is not limited to any particular type of graft material whereby the graft material may be, for example, bone graft material or synthetic graft material. Example of a suitable synthetic graft material include calcium phosphate materials, hydroxyl apatite, collagen, and both resorbable and non-resorbable polymers. The invention may use other synthetic graft materials currently existing or any future developed graft materials. Further, any suitable bone graft material may be used including cortical, cancellous, medullary, or any combination thereof, such as a combination of cancellous and cortical. Further, the bone graft materials may be autograft, allograft, zenograft, or genetically engineered graft materials. Moreover, the graft material may be any combination of graft materials, such as more than one bone graft material, bone graft materials and synthetic graft materials, or more than one synthetic graft material. Fresh-frozen grafts are commonly used but due to potential hazards with disease transfer other alternative graft sources may be desirable. At present, no clear consensus exists on the optimal source, shape, and size of the graft material. One recommended size is in the two to four millimeter range, although other sizes may be preferable. A bone mill may be used to prepare the graft material.

With reference to FIG. 3, graft material 25 is introduced into the medullary canal, such as with a graft delivery syringe 27. The graft delivery syringe 27 is desirable since it minimizes contamination with graft-bone in the surroundings. Next, as shown in FIG. 4, an additional amount of graft material 25 is introduced into the distal end of the medullary canal with a canal filler 29. The amount of graft material that is introduced depends upon the particular application and patient, but as one example may comprise five to ten cubic centimeters of graft material 25. The graft material 25 is impacted moderately over the guide wire 20 to ensure an easy introduction of radial impactors.

Next, a process of radially packing the medullary canal will be described with FIGS. 5(A) to 5(C). In contrast to packing the medullary canal in a distal direction, as is typical with conventional techniques, the medullary canal is packed in a radial direction toward the cortex of the bone. One way in which the medullary canal may be packed radially is with a series of radial impactors shown in FIGS. 5(A) to 5(C).

Figure 5A:
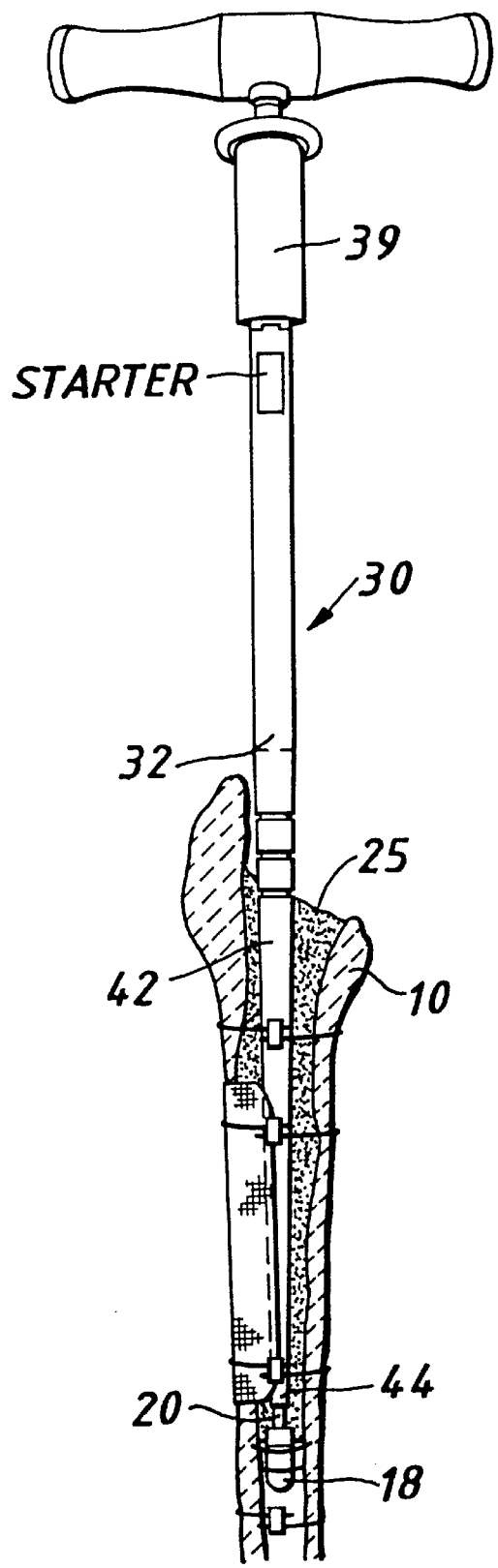

As shown in FIG. 5(A), a first radial impactor 30, which is illustrated as a starter radial impactor 32, is inserted into the medullary canal of the femur 10. The radial impactor 32 according to this example is cannulated and is guided by the guide wire 20 within the center of the femur 10. The radial impactor 32 has a working surface which is intended to be inserted within the medullary canal and to pack the medullary canal in the radial direction. Preferably, the working surface 42 is tapered at an insertion end 44 and has a circular cross-section. The radial impactors 30, however, need not have any taper and may have cross-section of other shapes. The working surface 42 is preferably one that reduces any distal packing of the medullary canal and instead maximizes an amount that the medullary canal is packed in the radial direction toward the cortex of the bone 10. The tapered working surface 42 is just one example of such a surface. The shapes, sizes, and other dimensions of the radial impactors 30 will be described in more detail with reference to FIGS. 10 to 12.

As discussed above, the radial impactors 30 are inserted into the medullary canal in order to pack the medullary canal in the radial direction toward the cortex. In the examples shown in FIGS. 5(A) to 5(C), the radial impactors 30 are used during a revision surgery to pack graft material 25 in the radial direction. The radial impactors 30 may accomplish packing of the graft material 25, or just packing of the medullary canal without graft material, in a variety of ways. For example, the insertion of the radial impactor 30 longitudinally into the medullary canal results in contact with the graft material 25 and directs the graft material 25 in the radial direction. The tapered insertion end 44 assists in the radial packing of the medullary canal as the impactor 30 is being inserted. The radial impactors 30 may be inserted with a handle 39 or with any other suitable mechanisms or devices. The radial impactors 30 may be driven into the medullary canal manually or with assistance, such as with a power driven instrument. Furthermore, the radial impactors 30 may be rotated with a drill motor to cause the medullary canal to be packed in the radial direction.

As shown in FIG. 5(B), a radial impactor 34 of a larger size than radial impactor 32 is then introduced into the medullary canal. The radial impactor 34 has outer peripheries that are larger than outer peripheries of the radial impactor 32 at corresponding positions along the length of the radial impactors 32 and 34. Thus, by introducing the larger sized radial impactor 34, the radial impactor 34 displaces an additional portion of the graft material in the radial direction. Additional radial impactors 30, such as radial impactor 36 shown in FIG. 5(C) may be inserted into the medullary canal to further pack the medullary canal in the radial direction. Preferably, progressively larger sized radial impactors 30 are used until a tight fight is achieved and until the size and length of the radial impactor 30 corresponds to dimensions of the prosthetic implant, such as a femoral stem.

Figure 6:
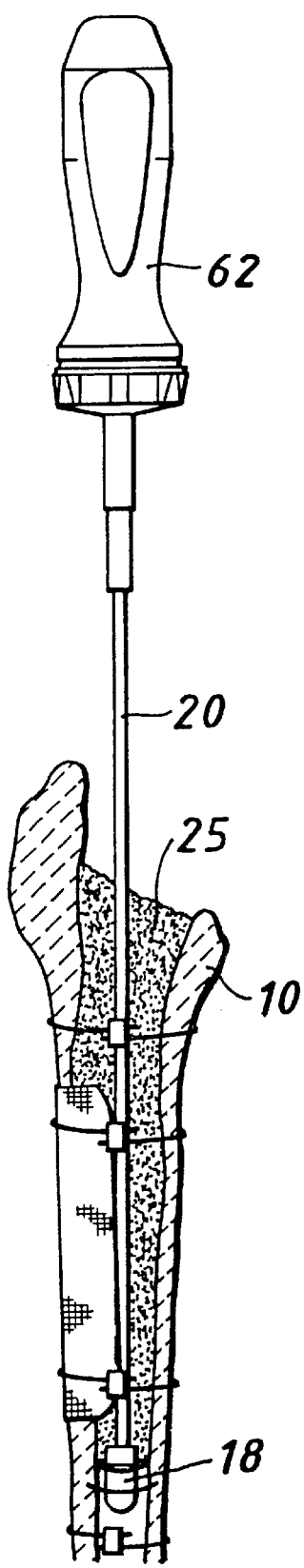
FIG. 6 is a partial schematic view of a femur and a guide rod which is inserted into the medullary canal and which is being removed with a ratchet handle.

With reference to FIG. 6, the central guide wire 20 is then preferably removed, such as with a ratchet handle 62. The guide wire 20 has a threaded end that is inserted into and possibly through the plug 18. The guide wire 20 is consequently rotated with the ratchet handle 62 in order to remove the guide wire 20 from the plug 18 and also from within the medullary canal. The plug 18 should remain within the medullary canal.

Following the insertion of the radial impactors 30, one or more profile impactors 70 may need to be introduced into the medullary canal. The profile impactors 70 may need to be introduced if, for example, the shape of the radial impactor 30 does not correspond to a shape of that portion of a prosthetic implant that is placed within the medullary canal of a host bone. If the shape of the prosthetic implant does correspond to that of the radial impactors 30, then only the radial impactors 30 may be needed to radially pack the medullary canal. Alternatively, instead of the radial impactors 30, the medullary canal may be packed only with a series of progressively larger profile impactors.

Figure 7A:
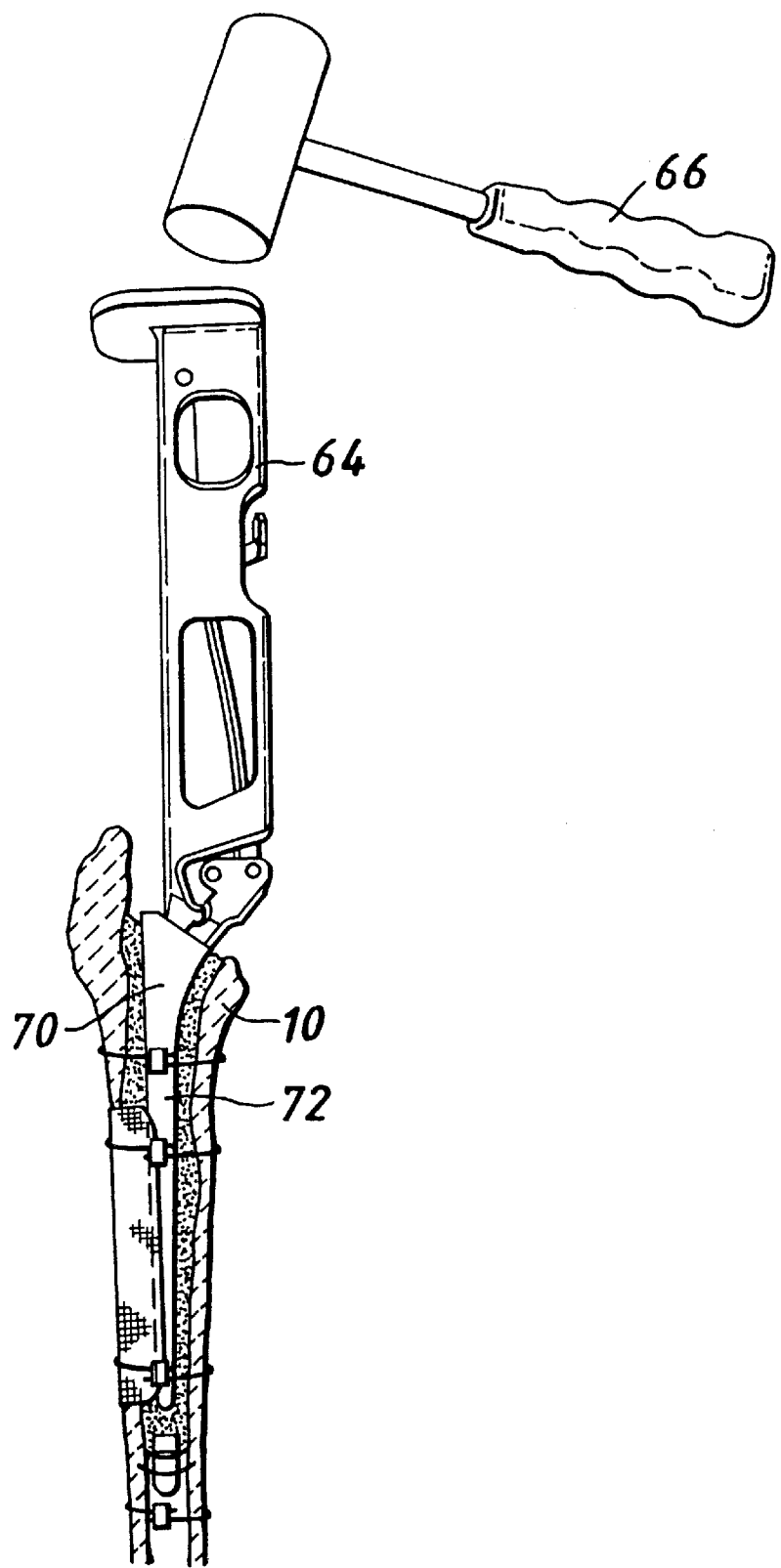
FIGS. 7(A) and 7(B) are partial schematic views of a femur having profile impactors of different sizes inserted into the medullary canal.
Figure 7B:
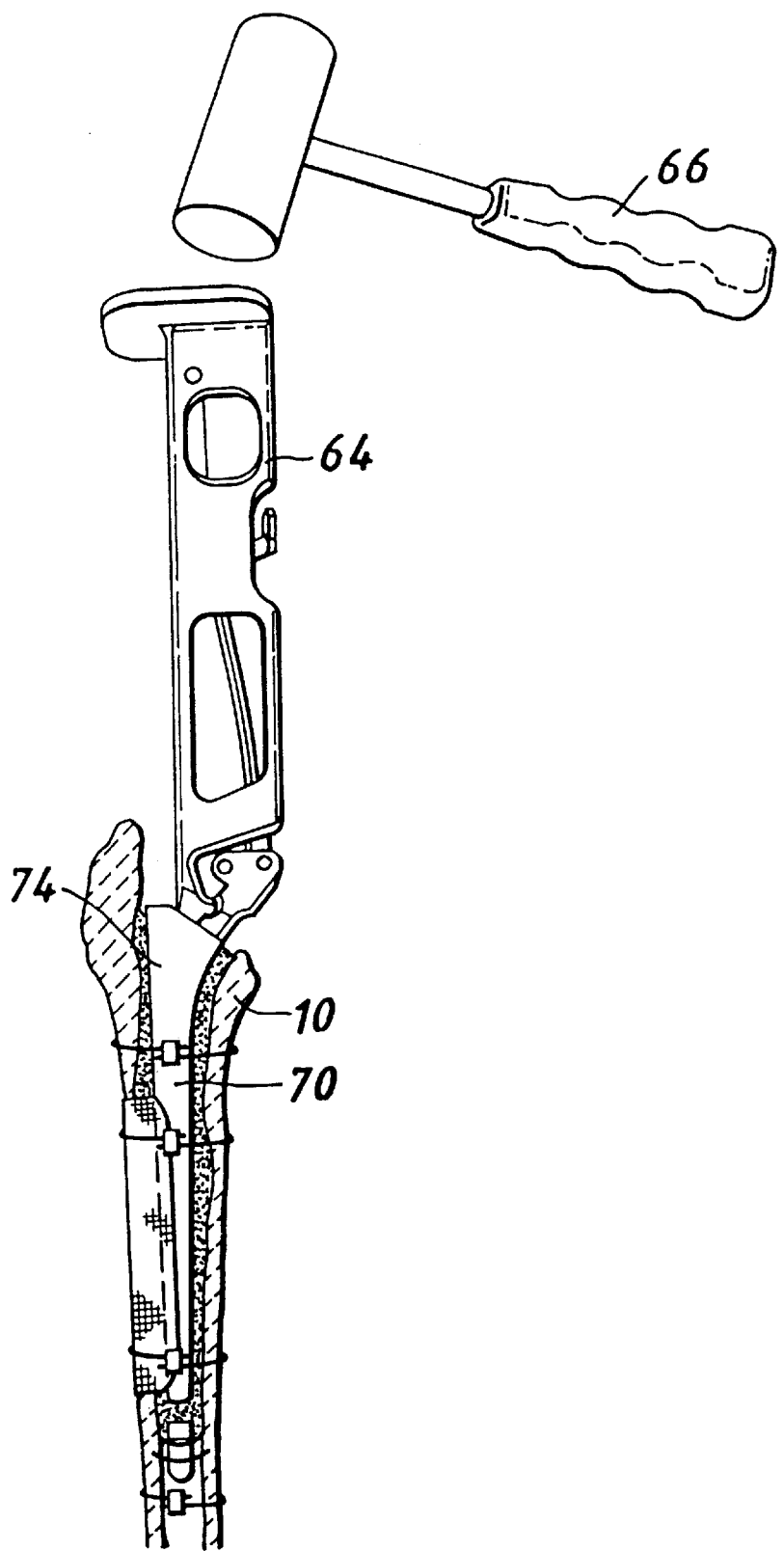
Figure 8:
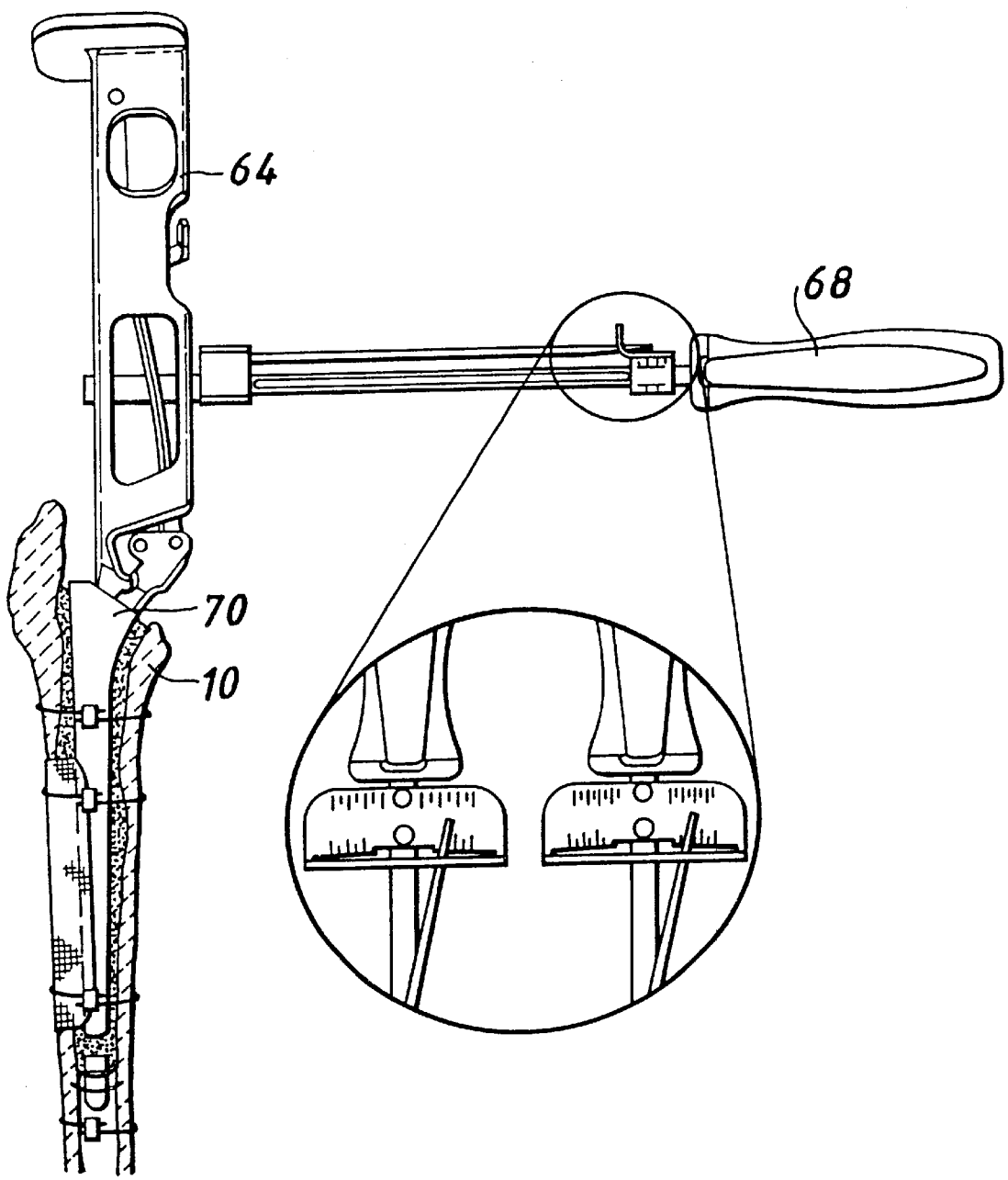
FIG. 8 is a partial schematic view of a femur having a profile impactor inserted and showing use of a torque wrench to measure stability.

FIGS. 7(A) and 7(B) illustrate profile impactors 70 that have a shape that generally corresponds to that portion of a femoral stem which is inserted into the medullary canal of a femur. According to a preferred technique, the profile impactor 70 is sized to correspond generally with the last used radial impactor 30. For instance, the radial impactors 30 used in FIGS. 5(A) to 5(C) correspond to a starter size, a size one, and a size two. A preferred size for the profile impactor 70 in this example would therefore be a size two profile impactor 70.

The profile impactors 70 may be inserted into the medullary canal in any suitable way. For example, as shown in FIG. 7(A), a broach handle 64 may be attached to the profile impactor 70 and may be used to transfer forces delivered from a mallet 66 to the profile impactor 70. The invention, of course, is not limited to this method of inserting the profile impactor 70. If the profile impactor 70 is not advancing down the medullary canal, then a smaller sized profile impactor 70 should be used with additional graft material 25 inserted into the medullary canal. The profile impactor 70 is advanced to a location within the medullary canal which corresponds generally to the final position of the prosthetic implant.

The profile impactor 70 may also be used to radially pack the medullary canal. FIG. 7(A) shows a profile impactor 72 of a first size while FIG. 7(B) shows a profile impactor 74 of a larger size. The user of progressively larger sized profile impactors 70 may be used in conjunction with progressively larger sized radial impactors 30 or instead of the radial impactors 30. As with the radial impactors 30, the insertion of progressively larger profile impactors 70 packs the medullary canal in the radial direction and prepares the host bone 10 for receipt of a prosthetic implant. In the examples of the profile impactors 30 shown in FIGS. 7(A) and 7(B), the profile impactors 70 are non-cannulated, however, as described below with reference to FIG. 19, the profile impactors 70 may be cannulated.

After the profile impactor 70 has been advanced to the desired location, stability of the host bone 10 and medullary canal is checked. According to a preferred way of checking stability, a torque wrench 68 is coupled to the broach handle 64 to measure a rotational stability of the profile impactor 70. The rotational stability is preferably within nine to eleven Newton-meters for both revision and primary cases. If additional stability is needed, one or more finishing tamps may be used to impact graft material 25 or portions of the medullary canal surrounding the profile impactor 70. Alternatively, additional use of radial impactors 30 or profile impactors 70 may be used to prepare the medullary canal for the prosthetic implant.

The torque wrench 68 allows the stability of the medullary canal to be checked objectively. Conventionally, surgeons pack the medullary canal to the best of their ability and usually have only subjective measurements as to whether the bone is sufficiently prepared. As a result, results in arthroplasty vary between surgeons and even vary between surgeries of a single surgeon. Use of the torque wrench 68, on the other hand, provides a clear and unambiguous indication as to whether the medullary canal has been packed sufficiently tight. Therefore, more uniform results and a higher rate of success in arthroplasty should be possible.

Figure 9:
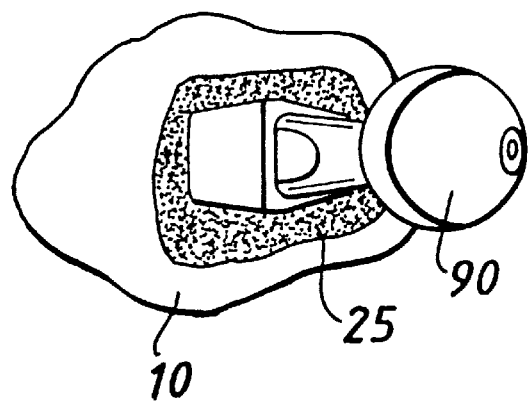
FIG. 9 is a top schematic view of a stem inserted into the medullary canal of a femur.

A prosthetic implant is then inserted into the medullary canal of the host bone. For example, as shown in FIG. 9, a femoral implant 90 is inserted into the femur 10 and is adjacent to graft material 25. The profile impactor 70 is preferably left in place until cement is ready to be introduced so as to avoid removing the packed graft material 25. A trial reduction with head-neck combinations may be conducted with the final profile impactor 70 in place until proper soft tissue tension, range of motion, and stability are achieved. The cement is mixed according to preferences of the surgeon following the handling instructions. For instance, a cement gun and retrograde filling may be used to introduce the cement. An extra-long and narrow nozzle may be required, in which case the cement should have a rather low viscosity at introduction. A prechilled cement may be used to facilitate the low viscosity. After filling the medullary canal with a cement, a proximal seal is applied and the cement is pressurized for approximately two to three minutes, with these directions varying with the handling instructions of the cement. The stem is preferably inserted with a stem driver and the proximal seal is maintained in place until the prosthetic implant is fully seated.

III. Exemplary Radial Impactors

Examples of suitable radial impactors 30 will now be described with reference to FIGS. 10 through 12. With reference to FIG. 10(A), a starter radial impactor 32 includes the working surface 42 and has an insertion end 44. In this example of the radial impactor 32, the starter radial impactor 32 is cannulated to have a bore or central aperture 45 along a length of the radial impactor 32. As discussed above, this bore or aperture 45 permits the radial impactor 32 to be guided by the guide wire 20.

The working surface 42 of the radial impactor is relatively smooth. The smooth working surface of the radial impactors 30 does not mean that the surface has to be free of any irregularities or completely polished. The working surface 42 should not be serrated, toothed, or similarly abrasive to the graft material or to the medullary canal of the host bone. The smooth working surfaces of the profile impactor and radial impactor 30 are contrasted with that of a broach or reamer which has teeth or other rough surfaces for abrasively removing portions of the medullary canal. The working surface 42 is smooth in the sense that contact between the radial packers 30 and graft material 25 or portions of the medullary canal will result in a radial packing of the medullary canal. A rough surface, on the other hand, would result in the capture of graft material within the irregular surface.

The radial impactors 30 preferably have a taper at the insertion end 44. The working surface 42 of the radial impactors 30, however, need not be tapered but instead the entire radial impactor may be cylindrical. A taper at the insertion end 44 is preferable since such a taper would minimize packing of the graft material 25 distally and instead promote radial packing of the medullary canal. The taper along the working surface 42 may be linear or may have other contours, such as a parabolic contour.

FIGS. 10 through 12 respectively show a starter radial impactor 32, a size two radial impactor 36, and a size four radial impactor 38. Each of the radial impactors 30 is approximately 11.75 inches long. The starter radial impactor 32 has an outer diameter of approximately 0.500 inches at a distance of 6.490 from the insertion end 44 and has an outer diameter of approximately 0.294 inches at 0.590 inches from the insertion end 44. Although not shown, a size one radial impactor 30 has an outer diameter of approximately 0.523 inches and 0.317 inches at the positions shown in FIGS. 10(B) and 10(C), respectively. The size two radial impactor 36, as shown in FIGS. 11(A) to 11(C), has outer peripheries greater than those of the starter 32 or size one radial impactors 30. The size two radial impactor 36 has an outer diameter of approximately 0.554 inches and a diameter of 0.348 inches at the positions of 6.490 inches and 0.590 inches, respectively, from the insertion end 44. A size three radial impactor 30 preferably has an outer diameter of 0.579 inches and an outer diameter of 0.373 inches at 6.490 inches and 0.590 inches, respectively, from the insertion end 44. The size four radial impactor 38, shown in FIGS. 12(A) to 12(C), preferably has an outer diameter of approximately 0.618 inches at 6.490 inches from the insertion end 44 and an outer diameter of approximately 0.412 inches at approximately 0.590 inches from the insertion end 44. The exact dimensions of the radial impactors 30 are not crucial to the invention and may be varied from that described. Further, the differences in outer peripheries may be greater or less than that shown and described with reference to radial impactors 30.

IV. Exemplary Profile Impactors

Figure 13A:
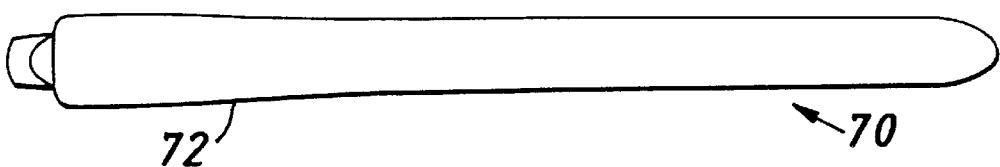
FIGS. 13(A), 13(B), and 13(C) are top, side, and cross-sectional views, respectively, of a profile impactor of a first size.
Figure 13B:
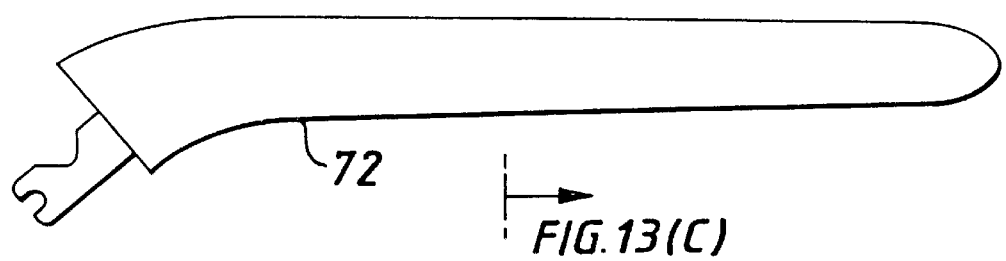
Figure 15A:
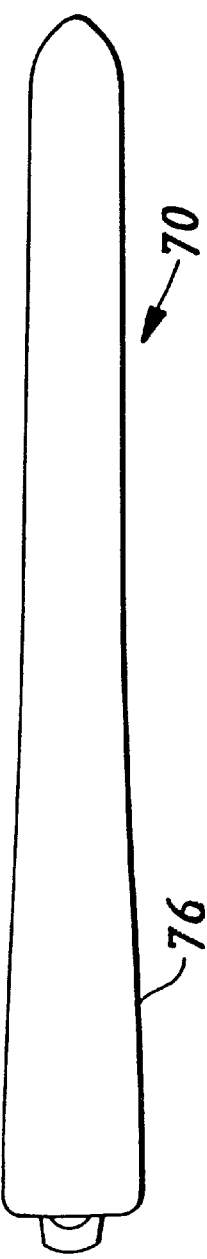
FIGS. 15(A), 15(B), and 15(C) are top, side, and cross-sectional views, respectively, of a profile impactor of a third size.
Figure 15B:
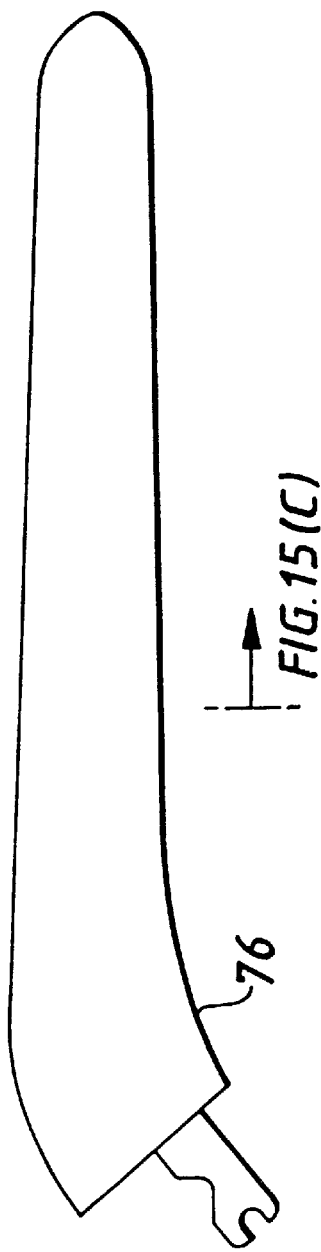

A series of progressively larger profile impactors 70 is shown in FIGS. 13 to 15. As is apparent from these figures, the general shape of each of the profile impactors 70 is the same and corresponds to that portion of the femoral implant that is inserted into the medullary canal of the femur 10. The profile impactors 70 also have a generally smooth working surface. As with the radial impactors 30, the smooth working surface of the profile impactors 70 does not mean that the surface has to be free of any irregularities or completely polished.

Figure 13C:
Figure 15C:

FIGS. 13 to 15 provide exemplary dimensions of suitable profile impactors 70. As is apparent from these figures, at the same location along a length of the profile impactors 70, the outer peripheries of the profile impactors become progressively larger. For example, at 2.362 inches from a non-insertion end of the profile impactors 70, a height of the profile impactor 70 varies from 0.555 inches shown in FIG. 13(C), to 0.651 inches shown in FIG. 14(C) to 0.747 inches shown in FIG. 15(C). The widths of the profile impactors 70 also become progressively larger from the profile impactor 72 shown in FIG. 13, to the profile impactor 74 shown in FIG. 14, to the profile impactor 76 shown in FIG. 15. The invention is not limited to the dimensions of the profile impactors shown in FIGS. 13 to 15 but rather may be varied to have greater or smaller variances between sizes.

V. Impactors with Primary Cases

A radial impactor 34' according to another embodiment of the invention is shown in FIG. 16. As discussed above, the radial impactor 30 is preferably cannulated and uses the guide wire 20 to center the radial impactor 30 within the bone. Alternatively, radial impactors 30' may be non-cannulated, such as radial impactor 34' shown in FIG. 16. Furthermore, the radial impactors 30 and 30' may be used in both primary surgeries and also with revision surgeries. FIG. 16 illustrates the radial impactor 34' being inserted into the medullary canal of the femur 10. The medullary canal of the femur 10, in contrast to that shown in FIGS. 5(A) to 5(C), does not include any graft material. The radial impactors 30 and 30' therefore may be used to pack the medullary canal of a bone and does not require the introduction of graft material into the host bone.

VI. Applications to other bones

The methods, instruments, and techniques according to the invention are not limited to just the femur 10. Instead, the invention may be applied to any long bone in the body including, but not limited to, the tibia, radius, ulna, humerus, or fibula. Furthermore, the invention is not limited to bones of a particular size but may be applied to some of the smaller bones within the body, such as those within the fingers or toes.

An example of an application of the invention to a bone other than the femur is shown in FIG. 17. With reference to FIG. 17, a radial impactor 36' is shown inserted into the medullary canal of a tibia 10'. In this example, graft material 25 is added to the tibia 10' and the radial impactor 36' is cannulated and is guided by a guide wire 20'. An intramedullary plug 18' is positioned within the medullary canal of the tibia 10'. After using a radial impactor 36' of a first size, progressively larger sized radial impactors are used until the approximate size of the implant is reached. The use of additional profile impactors may be necessary, such as if the radial impactors do not correspond in shape to the prosthetic implant.

VII. Alternate Embodiments of Radial and Profile Impactors

Figure 18:
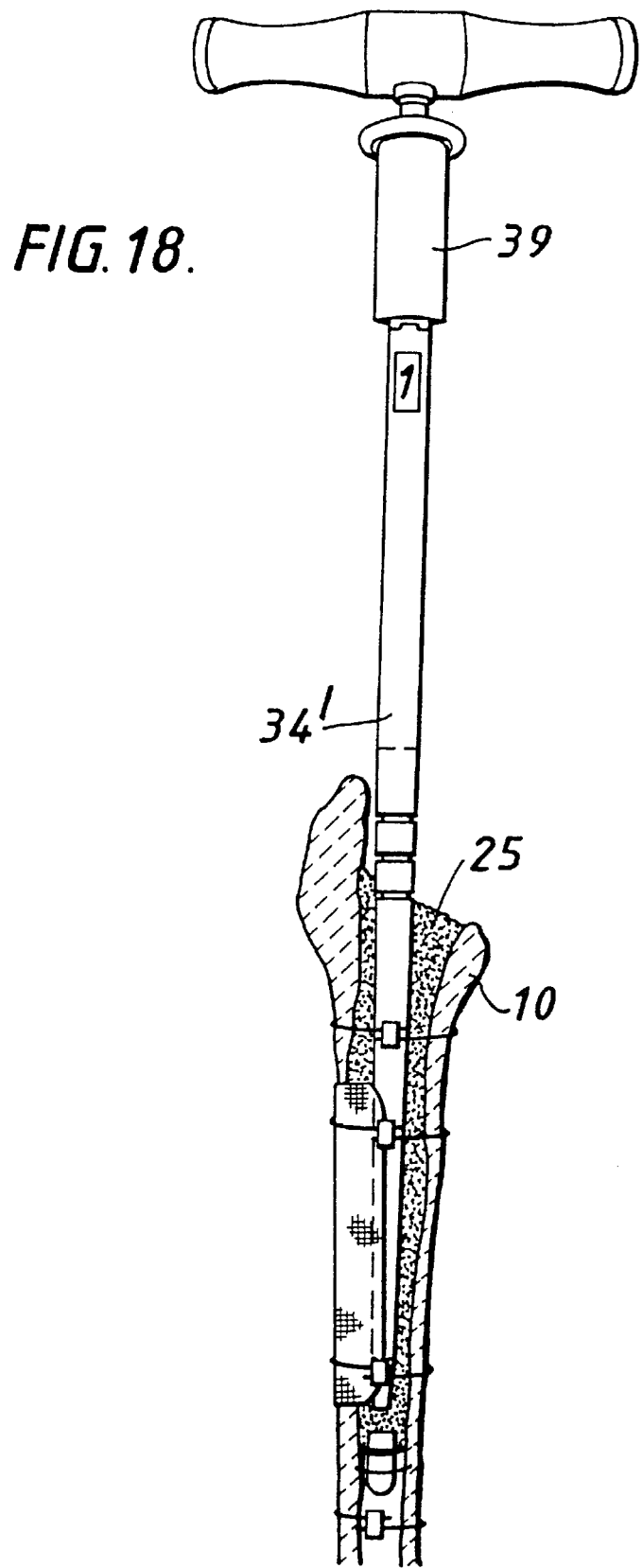
FIG. 18 is a partial schematic view of a femur and radial impactor according to a second embodiment of the invention, the radial impactor not being cannulated.

FIG. 18 illustrates the use of the radial impactor 34' in a revision case. The radial impactor 34' was described in connection with FIG. 16, which illustrates the radial impactor 34' was described in connection with FIG. 16, which illustrates the radial impactor 34' being inserted into the femur 10 during a primary case without any graft material. FIG. 18 illustrates another possibility in which the non-cannulated radial impactor 34' is used during a revision in which graft material 25 is added to within the medullary canal of the bone 10. Thus, the radial impactors according to the invention may be used in either primary or revision cases, may be cannulated or non-cannulated, and may be used with or without graft material.

Figure 19:
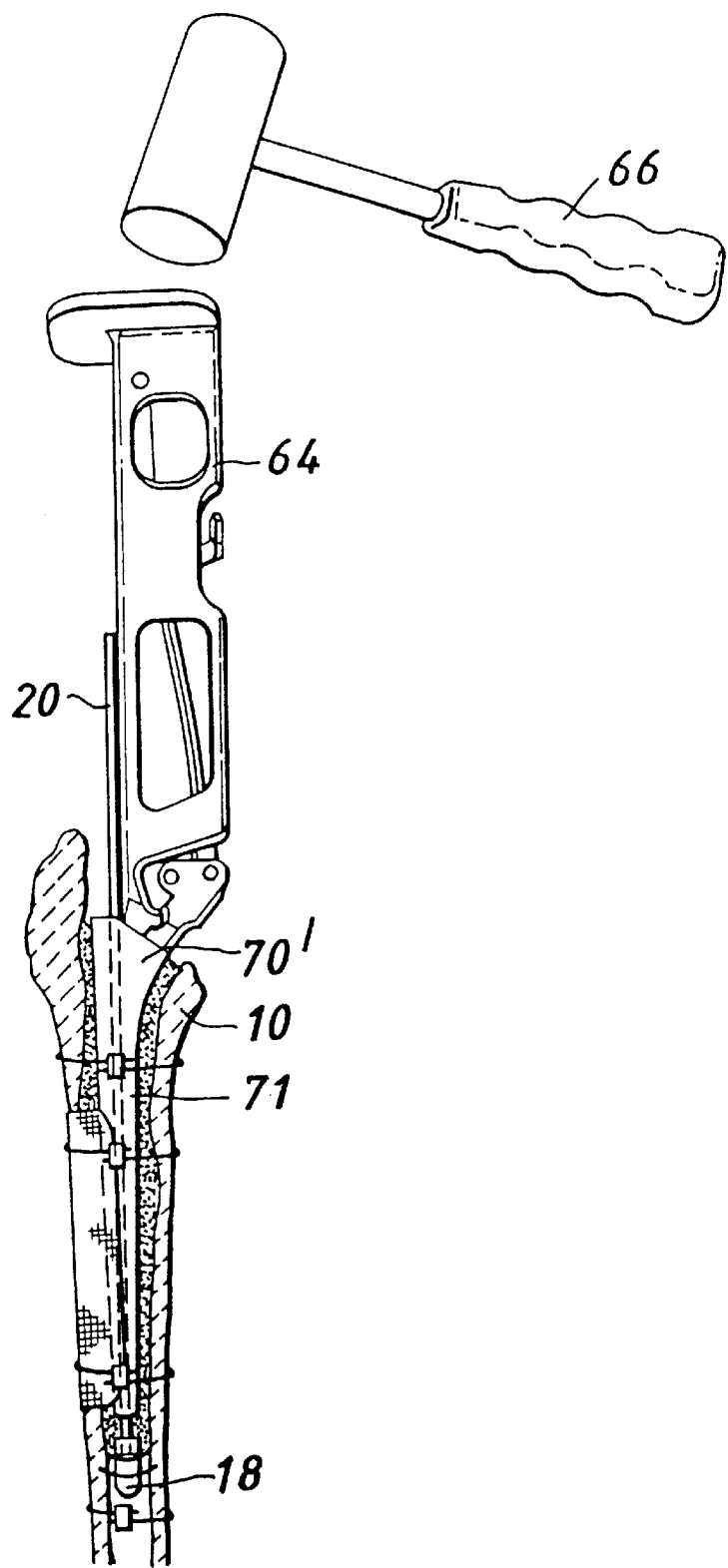
FIG. 19 is a partial schematic view of a femur and a profile impactor according to a second embodiment of the invention, the profile impactor being cannulated.

The profile impactors according to the invention may also be used in primary or revision cases, may be cannulated or non-cannulated, and may be used with or without graft material. For example, FIG. 19 illustrates a profile impactor 70' which is cannulated and is guided by the guide wire 20 into the medullary canal of the femur 10. Thus, the guide wire 20 would not be removed after the radial impactors have been inserted but would remain in place during the insertion of the one or more profile impactors 70'.

The graft material that is typically used is comprised of particulate matter and also includes some liquid, such as water or blood. In packing the graft material into the host bone, some of the liquid may remain between the particulate matter of the graft material and some may pool within the medullary canal. The presence of this liquid may render it difficult to pack the medullary canal sufficiently tight.

The radial impactors and profile impactors according to another embodiment of the invention may be cannulated and may include a plurality of apertures extending through to a central bore or aperture. FIGS. 20(A) and 20(B) provide an example of a radial impactor 80 having plural holes 82. These holes 82 extend from an outer working surface of the impactor 80 to a central bore or aperture 85 extending along the length of the impactor 80. As shown in FIG. 20(A), the radial impactor 80 is preferably used to pack the medullary canal in the radial direction. The holes 82 preferably allow fluids within the graft material or other portions of the medullary canal to be removed from within the medullary canal and travel into the bore 85 of the impactor 80. Whereas before these fluids may form a barrier between the impactor and the medullary canal, the impactor 80 having the holes 82 permits the removal of the fluids so that the medullary canal may be packed more tightly.

As an option, as shown in FIG. 20(B), the radial impactor 80 may be connected to a mechanism 86 for removing the fluids from within the medullary canal. For example, the radial impactor 80 may be connected to tubing 84 and to a removal mechanism 86. The removal mechanism 86 draws or otherwise forces fluids out of the medullary canal whereby the medullary canal may be packed more densely. The removal mechanism 86 may create a vacuum or suction to pull the fluids up through the radial impactor 80 and out of the medullary canal of the host bone 10. It should be understood that fluid that has entered the radial impactor 80 may be withdrawn in a variety of ways other than that disclosed herein.

VIII. Alternate Methodology

As described above with reference to packing of the femoral canal, progressively larger sized radial packers are used to radially pack the medullary canal. In some situations, it may be preferably to pack a medullary canal using progressively smaller radial impactors. For example, the tibia is a relatively long and cylindrical bone that may contain some rather large defects in the cortical wall. A relatively large sized radial impactor may be used first to pack graft material into these large defects followed by one or more smaller radial impactors to ensure proper coverage. After these large defects have been packed, smaller sized radial impactors may subsequently be used to complete the radial packing process. These smaller sized radial impactors may then be used in order from small to large to ensure that the graft material is radially packed.

The forgoing description of the preferred embodiments of the invention has been presented only for the purpose of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated.

What is claimed is:

1. A method of preparing a medullary canal of a bone for receipt of a prosthetic implant by packing, graft material, comprising:
    inserting a first packer into the medullary canal to pack said graft material, the first packer comprising:
        (a) a first outer periphery at a reference position within the medullary canal and
        (b) a working surface having a substantially circular cross-section throughout its entire length;
    inserting at least a second packer into the medullary canal to pack said graft material, the second packer comprising:
        (a) a second outer periphery at the reference position and
        (b) a working surface having a substantially circular cross-section throughout its entire length, the second outer periphery being greater than the first outer periphery;
    wherein inserting the second packer occurs after inserting the first packer so as to pack the medullary canal in a radial direction toward the cortex of the bone.

2. The method as set forth in claim 1, further comprising inserting graft material into the medullary canal and wherein the inserting of the first and second packers packs the graft material in the radial direction toward the cortex of the bone.

3. The method as set forth in claim 2, wherein the inserting of the graft material comprises inserting a synthetic graft material.

4. The method as set forth in claim 2, wherein the inserting of the graft material comprises inserting a bone graft material.

5. The method as set forth in claim 1, further comprising withdrawing fluid from within the medullary canal through at least one of the first or second packer.

6. The method as set forth in claim 5, wherein the withdrawing includes withdrawing fluid through a plurality of apertures in the at least one of the first or second packer.

7. The method as set forth in claim 1, further including inserting a guide wire into the medullary canal.

8. The method as set forth in claim 7, wherein the first and second packers are cannulated and the inserting of the first and second packers includes passing the guide wire through the first and second packers.

9. The method as set forth in claim 1, further including inserting at least one profile packer into the medullary canal, a portion of the profile packer having a shape that approximates a shape of a prosthetic implant.

10. The method as set forth in claim 9, further including inserting a second profile packer into the medullary canal following the one profile packer, a portion of the second profile packer having a shape that approximates a shape of a prosthetic implant, the second profile packer having a profiled outer periphery greater than a profiled outer periphery of the one profile packer at corresponding positions along lengths of the one and second profile packers.

11. The method as set forth in claim 9, wherein the one profile packer is cannulated and the method further includes inserting a guide wire into the medullary canal and guiding the one profile packer with the guide wire.

12. The method as set forth in claim 9, wherein the one profile packer is non-cannulated and the method further includes removing a guide wire from within the medullary canal prior to inserting the one profile packer.

13. The method as set forth in claim 1, further including inserting the prosthetic implant into the medullary canal.

14. The method as set forth in claim 1, further including inserting a third packer into the medullary canal, the third packer having a third outer periphery at the reference position, the third outer periphery being greater than the first outer periphery and greater than the second outer periphery.

15. The method as set forth in claim 1, further including removing a previously installed prosthetic implant from within the medullary canal prior to inserting the first and second packers.

16. The method as set forth in claim 1, wherein the inserting of the first and second packers includes symmetrically packing the medullary canal.

17. The method as set forth in claim 1, wherein the inserting of the first and second packers comprises inserting the first and second packers into a femur.

18. The method as set forth in claim 1, wherein the inserting of the first and second packers comprises inserting the first and second packers into a tibia.

19. The method as set forth in claim 1, wherein the inserting of the first and second packers comprises inserting the first and second packers into a humerus.

20. The method as set forth in claim 1, further comprising measuring the stability of the medullary canal with a torque wrench.

21. The method as set forth in claim 1, wherein the inserting comprises inserting at least one of the first or second packers into the medullary canal with a power driven instrument.

22. The method as set forth in claim 1, further comprising rotating at least one of the first or second packers after insertion in the medullary canal.

23. A method of preparing a medullary canal of a bone for receipt of a prosthetic implant by packing graft material, comprising:
  inserting a first packer having an insertion end and working surface into the medullary canal, the working surface having a substantially circular cross-section throughout its entire length with the working surface generally decreasing in cross-section in a direction toward the insertion end;
  inserting at least a second packer having an insertion end and working surface into the medullary canal, the working surface of the second packer having a substantially circular cross-section throughout its entire length and generally decreasing in cross-section in a direction toward the insertion end, diameters of the second packer being larger than the diameters of the first packer at corresponding positions along lengths of the first and second packers;
  wherein inserting the first and second packers pack the medullary canal in a radial direction toward the cortex of the bone.

24. The method as set forth in claim 23, further comprising inserting graft material into the medullary canal and wherein the inserting of the first and second packers packs the graft material in the radial direction toward the cortex of the bone.

25. The method as set forth in claim 24, wherein the inserting of the graft material comprises inserting a synthetic graft material.

26. The method as set forth in claim 24, wherein the inserting of the graft material comprises inserting a bone graft material.

27. The method as set forth in claim 23, wherein inserting the first packer occurs before inserting the second packer.

28. The method as set forth in claim 23, wherein inserting the second packer occurs before inserting the first packer.

29. The method as set forth in claim 23, further comprising withdrawing fluid from within the medullary canal through at least one of the first or second packer.

30. The method as set forth in claim 29, wherein the withdrawing includes withdrawing fluid through a plurality of apertures in the at least one of the first or second packer.

31. The method as set forth in claim 23, further including inserting a guide wire into the medullary canal.

32. The method as set forth in claim 31, wherein the first and second packers are cannulated and the inserting of the first and second packers includes passing the guide wire through the first and second packers.

33. The method as set forth in claim 23, further including inserting at least one profile packer into the medullary canal, a portion of the profile packer having a shape that approximates a shape of a prosthetic implant.

34. The method as set forth in claim 33, further including inserting a second profile packer into the medullary canal following the one profile packer, a portion of the second profile packer having a shape that approximates a shape of a prosthetic implant, the second profile packer having a profiled outer periphery greater than a profiled outer periphery of the one profile packer at corresponding positions along lengths of the one and second profile packers.

35. The method as set forth in claim 33, wherein the one profile packer is cannulated and the method further includes inserting a guide wire into the medullary canal and guiding the one profile packer with the guide wire.

36. The method as set forth in claim 33, wherein the one profile packer is non-cannulated and the method further includes removing a guide wire from within the medullary canal prior to inserting the one profile packer.

37. The method as set forth in claim 23, further including inserting the prosthetic implant into the medullary canal.

38. The method as set forth in claim 23, further including inserting a third radial packer having a working surface and an insertion end into the medullary canal, at least part of the working surface having a circular cross-section and generally decreasing in cross-section in the direction toward the insertion end, wherein diameters of the third packer being larger than diameters of the first or second packer at corresponding positions along lengths of the first, second, and third packers.

39. The method as set forth in claim 23, further including removing a second prosthetic implant from within the medullary canal prior to inserting the first and second packers.

40. The method as set forth in claim 23, wherein inserting the first and second packers includes symmetrically packing the medullary canal.

41. The method as set forth in claim 23, wherein the inserting of the first and second packers comprises inserting the first and second packers into a femur.

42. The method as set forth in claim 23, wherein the inserting of the first and second packers comprises inserting the first and second packers into a tibia.

43. The method as set forth in claim 23, wherein the inserting of the first and second packers comprises inserting the first and second packers into a humerus.

44. The method as set forth in claim 23, further comprising measuring the stability of the medullary canal with a torque wrench.

45. The method as set forth in claim 23, wherein the inserting comprises inserting at least one of the first and second packers into the medullary canal with a power driven instrument.

46. The method as set forth in claim 23, further comprising rotating at least one of the first or second packers after insertion in the medullary canal.

47. A radial packer in combination with graft material for preparing a medullary canal for receipt of a prosthetic implant, comprising:
   a radial packer having a smooth working surface, the working surface having a substantially circular cross-section throughout its entire length that generally decreases in diameter at an insertion end, the insertion end adapted to be inserted into the medullary canal; and
   graft material for being inserted into the medullary canal, the graft material adapted to be packed by the packer in a radial direction relative to the medullary canal toward a cortex of the bone; and
   an instrument for being coupled to the radial packer for rotating the radial packer after the packer is inserted into the medullary canal in order to pack the graft material in the medullary canal.

48. The combination as set forth in claim 47, wherein the graft material includes synthetic material.

49. The combination as set forth in claim 47, wherein the graft material includes bone graft material.

50. The combination as set forth in claim 47, wherein the radial packer is cannulated.

51. The combination as set forth in claim 47, wherein the radial packer has a plurality of apertures.

52. The combination as set forth in claim 47, further including a profile packer having a working surface of circular cross-section that generally decreases in diameter at an insertion end, the insertion end adapted to be inserted into the medullary canal.

53. The combination as set forth in claim 47, further including the prosthetic implant adapted to be inserted into the medullary canal.

54. The combination as set forth in claim 47, further including a guide wire adapted to be inserted into the medullary canal.

55. A collection of instruments for preparing a bone for receipt of a prosthetic implant, comprising:
   a plurality of radial packers each having a smooth working surface adapted to pack the medullary canal in a radial direction toward the cortex of the bone, the radial packers being sized to have progressively larger outer peripheries at corresponding positions along the lengths of the radial packers and the radial packers each having a working surface having a substantially circular cross-section throughout its entire length;
   at least one profile packer adapted to pack the medullary canal to define an aperture within the medullary canal bone of an approximate size and shape to receive at least part of the prosthetic implant, and
   an instrument for being coupled to the radial packer for rotating the radial packer after the radial packer is inserted into the medullary canal in order to pack the graft material in the medullary canal.

56. The collection as set forth in claim 55, further including the prosthetic implant.

57. The collection as set forth in claim 55, wherein the radial packers are cannulated.

58. The collection as set forth in claim 55, wherein the at least one profile packer is cannulated.

59. The collection as set forth in claim 55, wherein the radial packers are non-cannulated.

60. The collection as set forth in claim 55, wherein the at least one profile packer is non-cannulated.

61. The collection as set forth in claim 55, further including a guide wire.

62. The collection as set forth in claim 55, further including a plurality of profile packers, a guide wire, the prosthetic implant, at least a second profile packer, a portion of the second profile packer having a shape that approximates a shape of a prosthetic implant, and at least one reamer.

63. The collection as set forth in claim 55, further including graft material.

64. A method of preparing a medullary canal for arthroplasty by packing graft material, comprising:
   inserting a guide wire into the medullary canal;
   inserting at least one cannulated radial packer to pack said graft material, the radial packer having an insertion end and working surface into the medullary canal, the working surface having a substantially circular cross-section throughout its entire length and generally decreasing in cross-section in a direction toward the insertion end; and
   inserting at least one profile packer into the medullary canal, a portion of the profile packer having a shape that approximates a shape of a prosthetic implant.

65. The method as set forth in claim 64, further comprising inserting the prosthetic implant into the medullary canal.

66. The method as set forth in claim 64, further comprising removing the guide wire prior to inserting the profile packer.

67. The method as set forth in claim 64, wherein inserting the at least one radial packer includes inserting a plurality of cannulated radial packers with radial packers having progressively larger outer peripheries at corresponding positions along lengths of the radial packers.

68. The method as set forth in claim 64, wherein inserting the at least one profile packer includes inserting a plurality of profile packers with successive profile packers having progressively larger outer peripheries at corresponding positions along lengths of the profile packers.

69. The method as set forth in claim 64, further comprising measuring the stability of the medullary canal with a torque wrench.

70. The method as set forth in claim 64, wherein the inserting comprises inserting the at least one radial impactor into the medullary canal with a power driven instrument.

71. The method as set forth in claim 64, further comprising rotating the at least one radial packer after insertion into the medullary canal.

72. A method of preparing a medullary canal for arthroplasty by packing graft material, comprising:

inserting at least one radial packer to pack the graft material, the radial packer having an insertion end and working surface into the medullary canal, the working surface having a substantially circular cross-section throughout its entire length and generally decreasing in cross-section in a direction toward the insertion end;

inserting at least one profile packer into the medullary canal, a portion of the profile packer having a shape that approximates a shape of a prosthetic implant; and inserting a prosthetic implant into the medullary canal.

73. The method as set forth in claim 72, further including inserting a guide wire into the medullary canal and wherein inserting the at least one radial packer includes inserting a cannulated radial packer.

74. The method as set forth in claim 72, wherein inserting the at least one radial packer includes inserting a plurality of radial packers with successive radial packers having progressively larger outer peripheries at corresponding positions along lengths of the radial packers.

75. The method as set forth in claim 72, wherein inserting the at least one profile packer includes inserting a plurality of profile packers with successive profile packers having progressively larger outer peripheries at corresponding positions along lengths of the profile packers.

76. The method as set forth in claim 72, further comprising measuring the stability of the medullary canal with a torque wrench.

77. The method as set forth in claim 72, wherein the inserting comprises inserting the at least one radial impactor into the medullary canal with a power driven instrument.

78. The method as set forth in claim 72, further comprising rotating the at least one radial packer after insertion into the medullary canal.

79. A collection of instruments for use in performing arthroplasty, comprising:

at least one radial packer adapted to be inserted into a medullary canal for packing graft material, each radial packer having a working surface that is generally tapered and having a substantially circular cross-section throughout its entire length, an insertion end of the radial packer having a smaller outer periphery than an outer periphery of a more distal position along a length of the radial packer;

a stem implant having a portion adapted to be inserted into the medullary canal; and an instrument for being coupled to the radial packer for rotating the radial packer after the radial packer is inserted into the medullary canal in order to pack the graft material in the medullary canal;

wherein outer peripheries of the at least one radial packer are smaller than outer peripheries of the stem implant at corresponding positions along lengths of the at least one radial packer and stem implant.

80. The collection of instruments as set forth in claim 79, wherein the at least one radial packer is cannulated.

81. A radial packer in combination with graft material for preparing a medullary canal for receipt of a prosthetic implant, comprising:

a radial packer having a smooth working surface, the working surface having a substantially circular cross-section throughout its entire length that generally decreases in diameter at an insertion end, the insertion end adapted to be inserted into the medullary canal;

graft material for being inserted into the medullary canal, the graft material adapted to be packed by the packer in a radial direction relative to the medullary canal toward the cortex; and a torque wrench for measuring the stability of an implant.

82. A collection of instruments for preparing a bone for receipt of a prosthetic implant, comprising:

a plurality of radial packers each having a smooth working surface adapted to pack the medullary canal in a radial direction toward the cortex of the bone, the radial packers being sized to have progressively larger outer peripheries at corresponding positions along the lengths of the radial packers and the radial packers each having a working surface having a substantially circular cross-section throughout its entire length;

at least one profile packer adapted to pack the medullary canal to define an aperture within the medullary canal bone of an approximate size and shape to receive at least part of the prosthetic implant; and a torque wrench for measuring the stability of an implant.

83. A method of preparing a medullary canal of a bone for receipt of a prosthetic implant by packing graft material, comprising:

inserting a packer having a working surface into the medullary canal to pack said graft material, the working surface of the packer having a substantially circular cross-section throughout its entire length, and rotating the radial packer for a continuous period of time in one direction, wherein the inserting the packer packs the medullary canal in a radial direction toward the cortex of the bone.

\* \* \* \* \*